United States Patent
Parker

(10) Patent No.: US 10,335,461 B2
(45) Date of Patent: Jul. 2, 2019

(54) INTERFERON THERAPY

(71) Applicant: FKD Therapies Limited, Chinnor (GB)

(72) Inventor: Nigel Parker, Chinnor (GB)

(73) Assignee: Trizell Limited, Chinnor (GB)

( * ) Notice: Subject to any disclaimer, the term of this patent is extended or adjusted under 35 U.S.C. 154(b) by 0 days.

(21) Appl. No.: 15/430,456

(22) Filed: Feb. 11, 2017

(65) Prior Publication Data

US 2017/0232071 A1   Aug. 17, 2017

Related U.S. Application Data

(60) Provisional application No. 62/295,268, filed on Feb. 15, 2016.

(51) Int. Cl.
| | |
|---|---|
| *A61K 38/21* | (2006.01) |
| *A61K 39/00* | (2006.01) |
| *A61K 39/02* | (2006.01) |
| *A61K 39/12* | (2006.01) |
| *A61K 39/39* | (2006.01) |
| *A61K 39/395* | (2006.01) |
| *A61K 48/00* | (2006.01) |
| *C07K 16/30* | (2006.01) |
| *A61K 47/60* | (2017.01) |
| *C07K 16/28* | (2006.01) |
| *A61P 35/00* | (2006.01) |
| *C12N 15/86* | (2006.01) |

(52) U.S. Cl.
CPC ........ *A61K 38/212* (2013.01); *A61K 39/0011* (2013.01); *A61K 39/02* (2013.01); *A61K 39/12* (2013.01); *A61K 39/39* (2013.01); *A61K 39/39558* (2013.01); *A61K 47/60* (2017.08); *A61K 48/005* (2013.01); *A61P 35/00* (2018.01); *C07K 16/2818* (2013.01); *C07K 16/30* (2013.01); *C07K 16/3023* (2013.01); *C07K 16/3061* (2013.01); *C12N 15/86* (2013.01); *A61K 2039/505* (2013.01); *A61K 2039/545* (2013.01); *A61K 2039/55561* (2013.01); *A61K 2039/55583* (2013.01); *A61K 2039/57* (2013.01); *C07K 2317/24* (2013.01); *C07K 2317/52* (2013.01); *C07K 2317/73* (2013.01); *C12N 2710/10343* (2013.01)

(58) Field of Classification Search
None
See application file for complete search history.

(56) References Cited

U.S. PATENT DOCUMENTS 7,691,822 B2 *  4/2010  Benedict .............. A61K 9/0034
                                           514/44 R
9,988,452 B2 *  6/2018  Freeman ............ C07K 16/2827

OTHER PUBLICATIONS

Bauer et al Human TLR9 confers responsiveness to bacterial DNA via species-specific CpG motif recognition PNAS Jul. 31, 2001 vol. 98 No. 16 9237-9242.*
Matsumoto et al TLR3: Interferon induction by double-stranded RNA including poly(I:C) Advanced Drug Delivery Reviews 60 (2008) 805-812.*
Powles et al MPDL3280A (anti-PD-L1) treatment leads to clinical activity in metastatic bladder cancer pp. 558-562 | N AT U R E | vol. 515 | Nov. 27, 2014.*
Parker et al 2016, Antitumour actions of interferons: implications for cancer therapy Nature Reviews | Cancer pp. 131-144.*
Sharpe et al 2007; The function of programmed cell death 1 and its ligands in regulating autoimmunity and infection; pp. 239-245.*
Stagg et al., Anti-ErbB-2 mAb therapy requires type I and II interferons and synergizes with anti-PD-1 or anti-CD137 mAb therapy; 7142-7147 | PNAS | Apr. 26, 2011 | vol. 108 | No. 17.*
Schreiner, B. et al. Interferon-β enhances monocyte and dendritic cell expression of B7—H1 (PD-L1), a strong inhibitor of autologous T-cell activation:relevance for the immune modulatory effect in multiple.*
Sollitto, Robert B., "Failure of Interferon Alfa and Isotretinoin Combination Therapy in the Nevoid Basal Cell Carcinoma Syndrome", Arch Dermatol., 1996, p. 94, VI32.*
Vilmer, C., "Failure of Isotretinoin and Interferon-a Combination Therapy for HPV-Linked Severe Vulvar Dyslpasia: A Report of Two Cases", The Journal of Reproductive Medicine, 1998, Abstract Only.
Sollitto, Robert B., "Failure of Interferon Alfa and Isotretinoin Combination Therapy in the Nevoid Basal Cell Carcinoma Syndrome", Arch Dermatol., 1996, p. 94, V132.

* cited by examiner

Primary Examiner — Maria G Leavitt
(74) Attorney, Agent, or Firm — Pharmaceutical Patent Attorneys, LLC

(57) ABSTRACT

Interferon therapy is improved by concomitant administration of an agent which minimizes the ability of interferon to up-regulate expression of Programmed Cell Death Protein 1 (also known as CD279).

16 Claims, 20 Drawing Sheets

INTERFERON THERAPY

RELATED APPLICATIONS

This application asserts priority from provisional patent filing U.S. Ser. No. 62/295,268, filed 15 Feb. 2016, the contents of which are here incorporated by reference.

FEDERALLY-SPONSORED RESEARCH & DEVELOPMENT

None.

JOINT RESEARCH AGREEMENT

Applicant has research agreements with inter alia M.D. Anderson Cancer Center (Houston, Tex.) and The Mayo Clinic (Rochester, Minn.) for work related to this application.

SEQUENCE LISTING

None.

PRIOR PUBLIC DISCLOSURES BY THE/AN INVENTOR

None.

BACKGROUND

Interferon has many clinical benefits. For example, interferon is known to up-regulate the immune system. It thus is potentially useful for recruiting the patient's innate immune system to identify and attack cancer cells. Interferon's efficacy as an anti-cancer agent, however, has to date proven wanting. This has been puzzling.

For example, the most effective bladder cancer treatment currently approved in The United States is intra-urethral Bacillus Calmette-Guérin vaccine. The antigenic vaccine is thought to stimulate bladder cells to express interferon, which in turn recruits the patient's innate immune system to better recognize cancer cell surface antigens and attack cancer cells. In over a third of cases, however, the vaccine is ineffective.

Similarly, intravesical instillation of exogenously manufactured interferon polypeptide has been tested to treat bladder cancer, but has been found less effective than expected.

I have discovered why, and figured out how to fix it.

BRIEF DESCRIPTION

I have found that interferon (either exogenously administered or expressed in response to a vaccine or other agent which up-regulates endogenous expression), in addition to stimulating interferon expression, also stimulates the expression of Programmed Cell Death Protein 1, also known as CD279. I have thus identified a previously-unrecognized adverse side effect of interferon therapy: interferon advantageously stimulates certain aspects of the patient's immune system, yet also up-regulates expression of Programmed Cell Death Protein 1. The resulting increase in Programmed Cell Death Protein 1 in turn down-regulates protective T cell function. This impairs the effectiveness of T cells in identifying and attacking cells bearing cancer cell-surface antigen. Thus, interferon produces two conflicting actions: it both increases immune system activity, yet inhibits the ability of the immune system to identify cancer cell-surface antigens.

I thus propose improving interferon therapy by co-administering an agent which inhibits the expression of Programmed Cell Death Protein 1. This will enable interferon to more fully achieve its therapeutic potential.

DETAILED DESCRIPTION

Interferon Therapy

Figure 1:
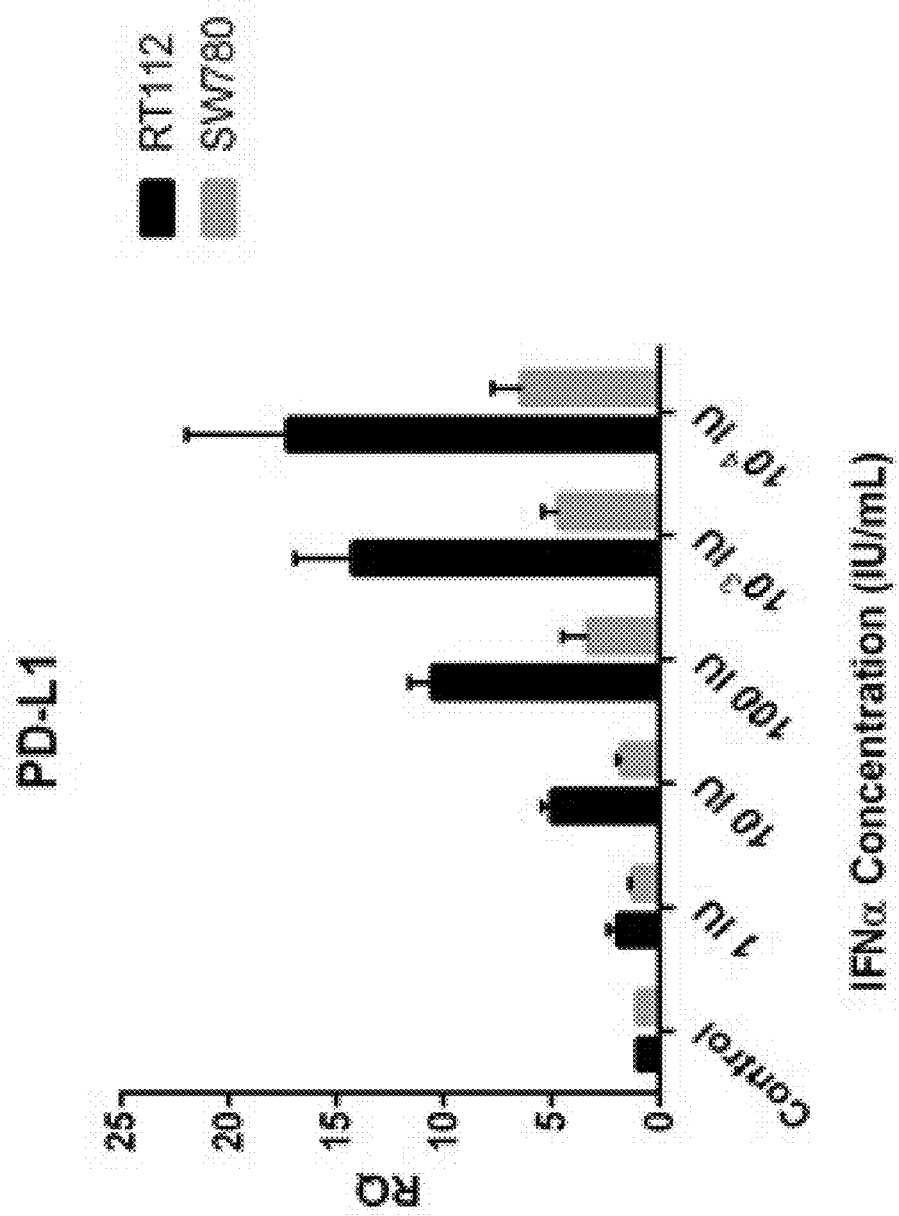
FIG. 1 is a chart measuring PD-L1 expression in response to interferon exposure, for the RT112 and SW780 human cell lines. Horizontal axis: interferon amount. Vertical axis: polypeptide expressed.
Figure 2:
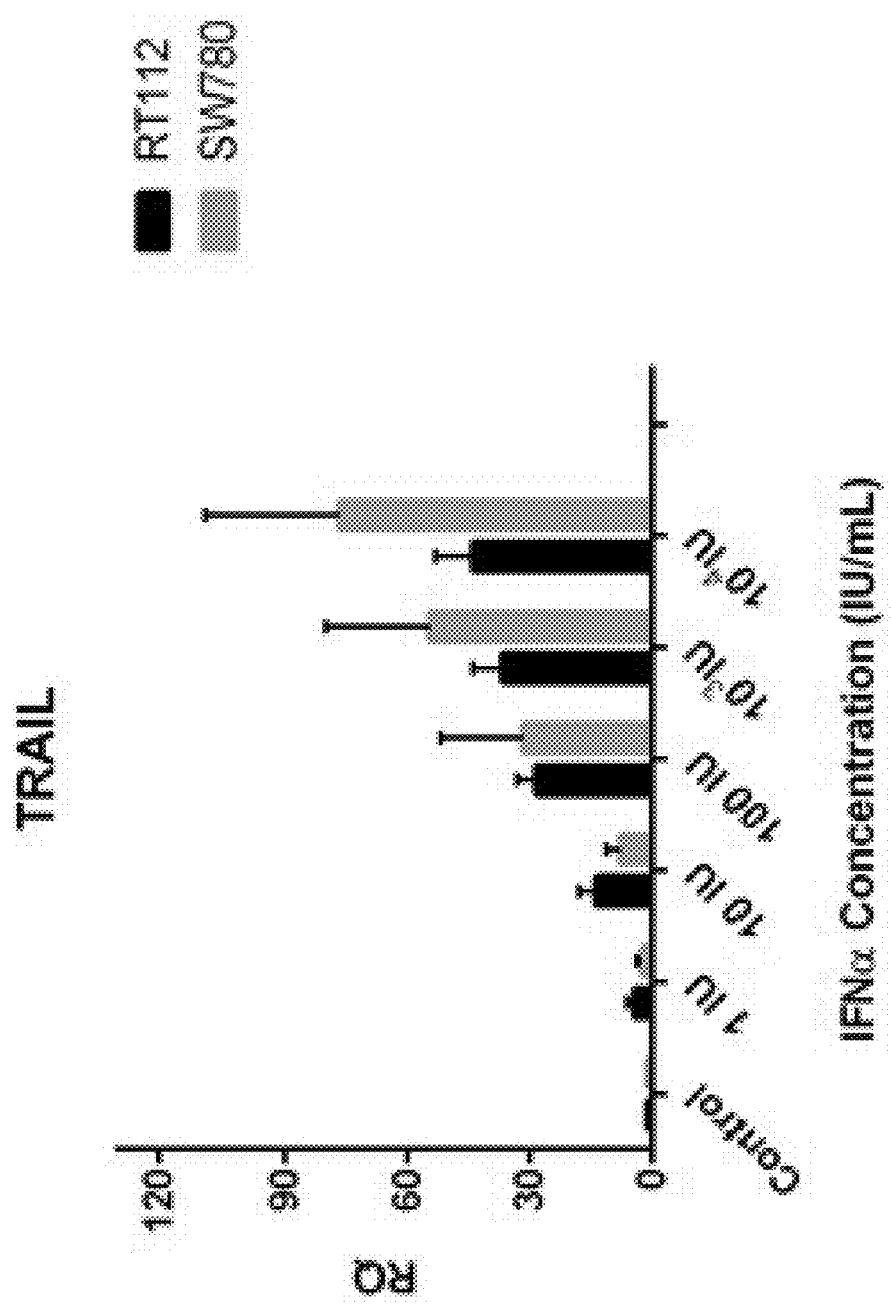
FIG. 2 is a chart measuring TRAIL expression in response to interferon exposure, for the RT112 and SW780 human cell lines. Horizontal axis: interferon amount. Vertical axis: polypeptide expressed.
Figure 3:
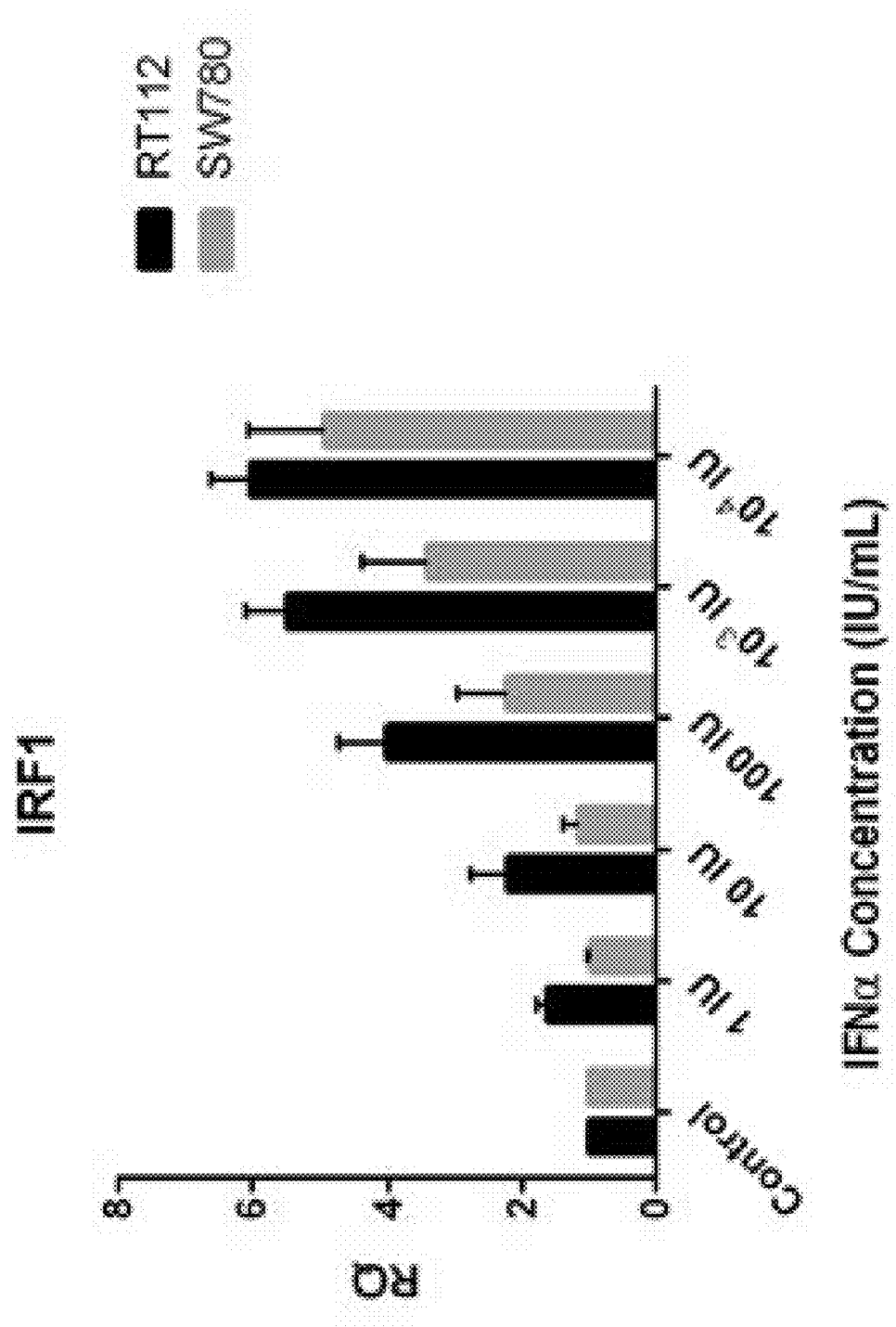
FIG. 3 is a chart measuring IRF1 expression in response to interferon exposure, for the RT112 and SW780 human cell lines. Horizontal axis: interferon amount. Vertical axis: polypeptide expressed.
Figure 4:
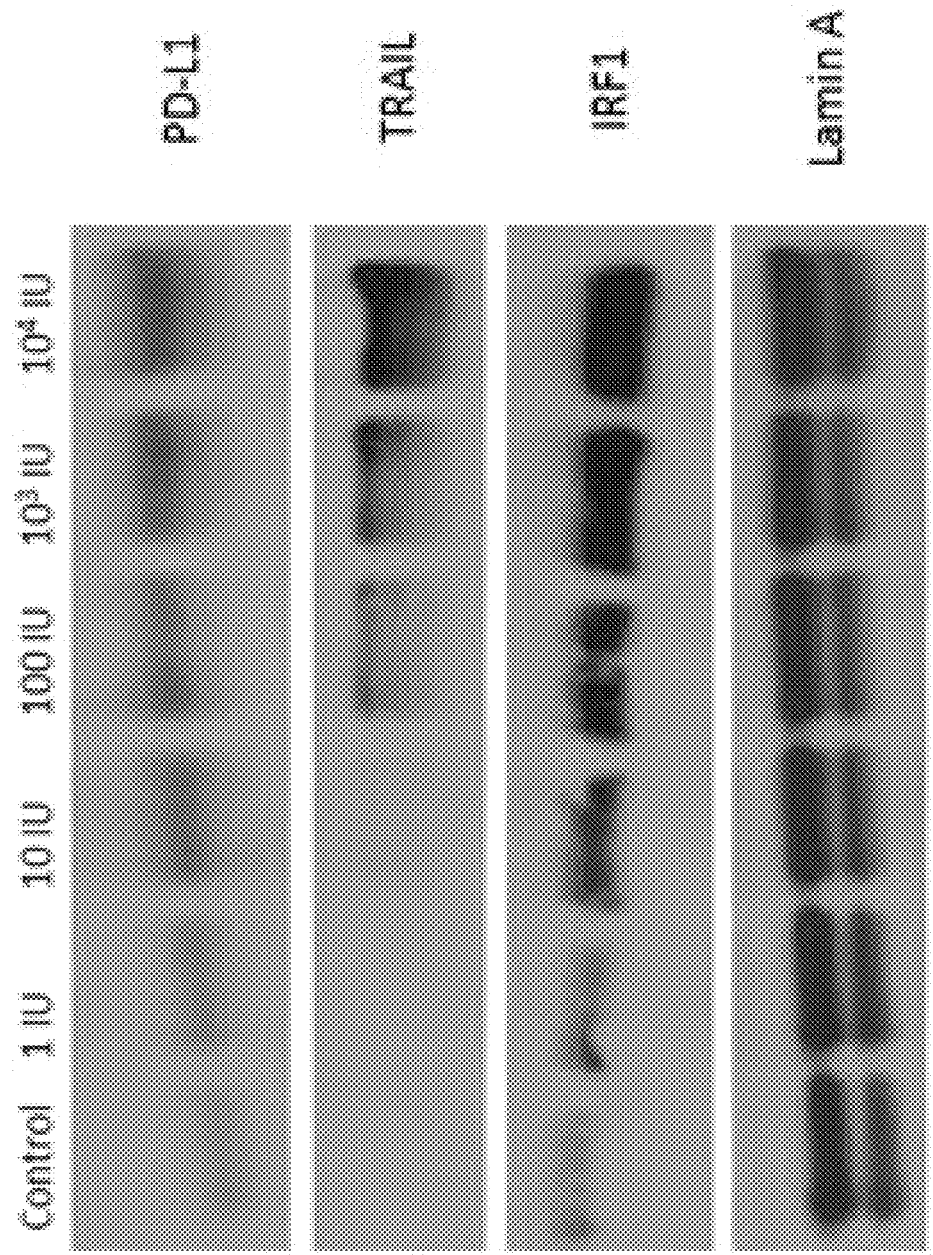
FIG. 4 is a photograph of a PAGE gel showing in vitro dose response to increasing interferon alpha, in an SW780 human cancer cell line. Horizontal axis: interferon amount. Vertical axis: polypeptide expressed.

Interferons are a group of signaling proteins. They are expressed and secreted by human cells in response to the presence of several antigenic pathogens, e.g., viruses, bacteria and parasites, and also tumor cells. Typically, a virus-infected cell releases interferons, signaling nearby bystander cells to heighten their anti-viral defenses. Interferons also activate immune cells such as natural killer cells and macrophages. Interferons increase expression of major histocompatibility complex antigens, which in turn increases presentation of foreign antigens to the immune system.

Interferons may be sorted or classified according to the type of receptor through which they signal. For humans, interferons are often thus sorted into three kinds: Type I (interferons which bind to human IFN-α/β receptors), Type II (interferons which binds to the human IFN-γ receptor) and Type III (interferons which bind to human IFN-λ receptors).

All interferons share several common effects: they are antiviral agents and they modulate functions of the immune system. Administration of Type I IFN has been shown to inhibit tumor growth in experimental animals, but the beneficial action in human tumors has not been widely documented. A virus-infected cell releases viral particles that can infect nearby cells. However, the infected cell can prepare neighboring cells against a potential infection by the virus by releasing interferons. In response to interferon, cells produce large amounts of an enzyme known as protein kinase R (PKR). This enzyme phosphorylates a protein known as eIF-2 in response to new viral infections; the phosphorylated eIF-2 forms an inactive complex with another protein, called eIF2B, to reduce protein synthesis within the cell. Another cellular enzyme, RNAse L—also induced by interferon action—destroys RNA within the cells to further reduce protein synthesis of both viral and host genes. Inhibited protein synthesis destroys both the virus and infected host cells. In addition, interferons induce production of hundreds of other proteins—known collectively as interferon-stimulated genes (ISGs)—that have roles in combating viruses and other actions produced by interferon. They also limit viral spread by increasing p53 activity, which kills virus-infected cells by promoting apoptosis. The effect of IFN on p53 is also linked to its protective role against certain cancers.

Another function of interferons is to up-regulate expression of major histocompatibility complex molecules, MHC I and MHC II, and increase immune-proteasome activity. Higher MHC I expression increases presentation of viral peptides to cytotoxic T cells, while the immune-proteasome processes viral peptides for loading onto the MHC I molecule, thereby increasing the recognition and killing of infected cells. Higher MHC II expression increases presentation of viral peptides to helper T cells; these cells release cytokines (such as more interferons and interleukins, among others) that signal to and co-ordinate the activity of other immune cells.

Production of interferons occurs mainly in response to microbes, such as viruses and bacteria, and their products. Binding of molecules uniquely found in microbes—viral glycoprotein, viral RNA, bacterial endotoxin (lipopolysaccharide), bacterial flagella, CpG motifs—by pattern recognition receptors, such as membrane bound Toll like receptors or the cytoplasmic receptors RIG-I or MDA5, can trigger release of IFNs. Toll Like Receptor 3 (TLR3) is important for inducing interferons in response to the presence of double-stranded RNA viruses; the ligand for this receptor is double-stranded RNA (dsRNA). After binding dsRNA, this receptor activates the transcription factors IRF3 and NF-kB, which are important for initiating synthesis of many inflammatory proteins. RNA interference technology tools such as siRNA or vector-based reagents can either silence or stimulate interferon pathways. Release of IFN from cells (specifically IFN in lymphoid cells) is also induced by mitogens. Other cytokines, such as interleukin 1, interleukin 2, interleukin-12, tumor necrosis factor and colony-stimulating factor, can also enhance interferon production.

Interferon therapy is used (in combination with chemotherapy and radiation) as a treatment for some cancers. This treatment can be used in hematological malignancy; leukemia and lymphomas including hairy cell leukemia, chronic myeloid leukemia, nodular lymphoma, and cutaneous T-cell lymphoma. Patients with recurrent melanomas receive recombinant IFN-α2b. Both hepatitis B and hepatitis C are treated with IFN-b, often in combination with other antiviral drugs. Some of those treated with interferon have a sustained virological response and can eliminate hepatitis virus. The most harmful strain-hepatitis C genotype I virus—can be treated with a 60-80% success rate with the current standard-of-care treatment of interferon, RIBAVIRIN™ and recently approved protease inhibitors such as Telaprevir (Incivek™) May 2011, Boceprevir (VICTRELIS™) May 2011 or the nucleotide analog polymerase inhibitor Sofosbuvir (SOVALDI™) December 2013. Biopsies of patients given the treatment show reductions in liver damage and cirrhosis. Some evidence shows giving interferon immediately following infection can prevent chronic hepatitis C, although diagnosis early in infection is difficult since physical symptoms are sparse in early hepatitis C infection. Control of chronic hepatitis C by IFN is associated with reduced hepato-cellular carcinoma.

The art teaches interferon may be administered as an exogenous polypeptide.

Alternatively, one may induce endogenous expression of native interferon genes. For example, the art teaches e.g., antigenic *Bacillus* Calmette-Guérin or *Mycobacterium* or Adenovirus vaccines. Such antigenic preparations induce the patient's own cells to express interferon.

Alternatively, one may induce endogenous expression of a non-native interferon transgene by transfecting a host cell with a vector delivering the interferon transgene. Indeed, even exogenously-administered interferon polypeptide itself acts as a messenger to stimulate interferon production.

As used herein, the term "interferon" (abbreviated "IFN") refers collectively to type 1 and type 2 interferons including deletion, insertion, or substitution variants thereof, biologically active fragments, and allelic forms. As used herein, the term interferon (abbreviated "IFN") refers collectively to type 1 and type 2 interferons. Type 1 interferon includes interferons-α, -β and -ω and their subtypes. Human interferon-α has at least 14 identified subtypes while interferon-β has 3 identified subtypes. Particularly, preferred interferon-alphas include human interferon alpha subtypes including, but not limited to, α-1 (GenBank Accession Number NP 076918), α-1b (GenBank Accession Number AAL35223), α-2, α-2a (GenBank Accession Number NP000596), α-2b (GenBank Accession Number AAP20099), α-4 (GenBank Accession Number NP066546), α-4b (GenBank Accession Number CAA26701), α-5 (GenBank Accession Numbers NP 002160 and CAA26702), α-6 (GenBank Accession Number CAA26704), α-7 (GenBank Accession Numbers NP 066401 and CAA 26706), α-8 (GenBank Accession Numbers NP002161 and CAA 26903), α-10 (GenBank Accession Number NP 002162), α-13 (GenBank Accession Numbers NP 008831 and CAA 53538), α-14 (GenBank Accession Numbers NP 002163 and CAA 26705), α-16 (GenBank Accession Numbers NP 002164 and CAA 26703), α-17 (GenBank Accession Number NP 067091), α-21 (GenBank Accession Numbers P01568 and NP002166), and consensus interferons as described in Stabinsky, U.S. Pat. No. 5,541,293, issued Jul. 30, 1996, Stabinsky, U.S. Pat. No. 4,897,471, issued Jan. 30, 1990, and Stabinsky, U.S. Pat. No. 4,695,629, issued Sep. 22, 1987, the teachings of which are herein incorporated by reference, and hybrid interferons as described in Goeddel et al., U.S. Pat. No. 4,414,150, issued Nov. 8, 1983, the teachings of which are herein incorporated by reference. Type 2 interferons are referred to as interferon γ (EP 77,670A and EP 146,354A) and subtypes. Human interferon gamma has at least 5 identified subtypes, including interferon omega 1 (GenBank Accession Number NP 002168). Construction of DNA sequences encoding inteferons for expression may be accomplished by conventional recombinant DNA techniques based on the well-known amino acid sequences referenced above and as described in Goeddel et al., U.S. Pat. No. 6,482,613, issued Nov. 19, 2002, the teachings of which are herein incorporated by reference.

"Biologically active" fragments of interferons may be identified as having any antitumor or anti-proliferative activity as measured by techniques well known in the art (see, for example, Openakker et al., supra; Mossman, *J. Immunol. Methods*, 65:55 (1983) and activate IFN responsive genes through IFN receptor mediated mechanisms. Soluble IFN-α and IFN-β proteins are generally identified as associating with the Type 1 IFN receptor complex (GenBank Accession Number NP 000865) and activate similar intracellular signaling pathways. IFN-γ is generally identified as associating with the type II IFN receptor. Ligand-induced association of both types of IFN receptors results in the phosphorylation of the receptors by Janus kinases subsequently activating STATs (signal transducers and activators of transcription) proteins and additional phosphorylation events that lead to the formation of IFN-inducible transcription factors that bind to IFN response elements presented in IFN-inducible genes. Polypeptides identified as activating the IFN pathways following association with Type 1 and/or Type 2 IFN receptors are considered interferons for purposes of our invention.

Programmed Cell Death Protein 1

Programmed Cell Death Protein 1 ("PD-1"), also known as CD279, is a protein that in humans is encoded by the PDCD1 gene. PD-1 belongs to the immunoglobulin superfamily and functions as a cell surface receptor, binding to two known ligands, PD-L1 and PD-L2.

PD-1 plays an important role in down-regulating the human immune system by preventing the activation of T cells, which in turn reduces autoimmunity and promotes "self-tolerance." The immune regulatory effect of PD-1 is effected by culling active T cells while protecting suppressor T cells. PD-1 promotes apoptosis of antigen-specific T cells in lymph nodes, yet reduces apoptosis in regulatory ("suppressor") T cells.

PD-L1 can be highly expressed in certain tumors. This leads to reduced proliferation of, or even elimination of, immune cells in the tumor, impairing the ability of the patient's innate immune system to recognize cancer cell-surface antigen and combat the cancer cells so identified.

PD-1 is expressed on T cells and pro-B cells. PD-1, functioning as an immune checkpoint, plays an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

Programmed death 1 is a type I membrane protein of 268 amino acids. PD-1 is a member of the extended CD28/CTLA-4 family of T cell regulators. The protein's structure includes an extracellular IgV domain followed by a transmembrane region and an intracellular tail. The intracellular tail contains two phosphorylation sites located in an immune-receptor tyrosine-based inhibitory motif and an immune-receptor tyrosine-based switch motif, which suggests that PD-1 negatively regulates TCR signals. This is consistent with binding of SHP-1 and SHP-2 phosphatases to the cytoplasmic tail of PD-1 upon ligand binding. In addition, PD-1 ligation up-regulates E3-ubiquitin ligases CBL-b and c-CBL that trigger T cell receptor down-modulation. PD-1 is expressed on the surface of activated T cells, B cells, and macrophages, suggesting that compared to CTLA-4, PD-1 more broadly negatively regulates immune responses.

PD-1 has two ligands, PD-L1 and PD-L2, which are members of the B7 family. PD-L1 protein is upregulated on macrophages and dendritic cells (DC) in response to LPS and GM-CSF treatment, and on T cells and B cells upon TCR and B cell receptor signaling, whereas in resting mice, PD-L1 mRNA can be detected in the heart, lung, thymus, spleen, and kidney.

Monoclonal antibodies targeting PD-1 that boost the immune system are being developed for the treatment of cancer. Many tumor cells express PD-L1, an immunosuppressive PD-1 ligand; inhibition of the interaction between PD-1 and PD-L1 can enhance T-cell responses in vitro and mediate preclinical antitumor activity. This is known as immune checkpoint blockade.

One such anti-PD-1 antibody drug, nivolumab, (OPDIVO™, commercially available from Bristol Myers Squibb Co., Princeton, N.J.), produced complete or partial responses in non-small-cell lung cancer, melanoma, and renal-cell cancer, in a clinical trial with a total of patients. Colon and pancreatic cancer patients did not have a response. Nivolumab (OPDIVO™, Bristol-Myers Squibb), which also targets PD-1 receptors, was approved in Japan in July 2014 and by the US FDA in December 2014 to treat metastatic melanoma.

Pembrolizumab (KEYTRUDA™ or MK-3475, commercially available from Merck & Co., Rahway, N.J.), which also targets PD-1 receptors, was approved by the FDA in September 2014 to treat metastatic melanoma. Pembrolizumab has been made accessible to advanced melanoma patients in the UK via UK Early Access to Medicines Scheme (EAMS) in March 2015. It is being used in clinical trials in the US for lung cancer, lymphoma, and mesothelioma. It has had measured success, with little side effects. On Oct. 2, 2015 Pembrolizumab was approved by FDA for advanced (metastatic) non-small cell lung cancer (NSCLC) patients whose disease has progressed after other treatments.

Other drugs in early stage development targeting PD-1 receptors (often referred to as "checkpoint inhibitors"): Pidilizumab (CT-011, Cure Tech), BMS 936559 (Bristol Myers Squibb), MPDL328OA (Roche), and atezolizumab (Amgen).

Combination Therapy

I have found that treatment of cancer with interferon—either by administering interferon polypeptide, or by administering an agent which induces cells to express interferon—concomitantly induces expression of PD-1.

I thus propose improving the efficacy of interferon-based cancer therapy by co-administering interferon with a compound which inhibits the activity of PD-1.

This entails, for example, administering interferon polypeptide intravenously in an amount effective as cancer therapy, and administering a monoclonal antibody checkpoint blockade inhibitor intravenously in an amount effective to prevent an interferon-caused increase in PD-1 expression, and preferably in an amount to reduce the effect of PD-1.

Alternatively, this entails instilling intravesically an agent which induces interferon expression, in an amount effective as cancer therapy, and prophylactically administering a checkpoint blockade inhibitor intravenously in an amount effective to prevent an interferon-caused increase in PD-1 expression, and preferably in an amount to reduce the effect of PD-1. The agent can be an antigenic vaccine (such as a virus, or BCG vaccine or *Mycobacterium* vaccine) which induces interferon expression. Alternatively, the agent can be a transgene vector which transforms a host cell with an expressible interferon transgene. Alternatively, this can be an antigenic virus or bacteria which also delivers an interferon transgene.

Example 1—IFNα Induces PD-L1 and TRAIL Expression

Interferon-alpha (IFNa) has not been notably effective clinically. I posited that this might be more effective in the setting of vector-mediated IFNa gene therapy. Several years ago, I began a phase II human clinical trial of INSTILADRIN™ brand adenovirus vector-mediated interferon alpha 2b. In this experiment, I had measured the expression of PD-L1, TRAIL, IRF1 and Lamin A in response to exposure to interferon.

Materials & Methods: RT112 and SW780 cells were cultured in media and then exposed to media containing interferon alpha polypeptide. The amount of interferon ranged from zero (control) to $10^4$ international units/mL. Gene expression was evaluated by Western blot and quantitative real-time PCR using commercially available antibodies and primers. RNA was isolated from cells in culture with the MIRVANA™ kit (Thermo Fisher). mIRs were profiled in RT112 using TAQMAN™ Array Cards (A and B) (Thermo Fisher). Whole genome mRNA expression profiling was performed in RT112 and UC3 with Illumina HumanHT_12_v4 BEADCHIP™ arrays (47323 probes).

Results: Results are provided in FIGS. 1 to 4. In response to exposure to interferon, both cell lines up-regulated PD-L1, TRAIL and IRF1 expression, and had no measurable effect on Lamin A expression. For PD-L1, TRAIL and IRF1 expression, the effect was of different magnitude in the different cell lines. See FIG. 1, 2, 3, 4.

Conclusions: In a panel of cancer cell lines, interferon exposure lead to significant increases in PD-L1 immune checkpoint expression. I found this finding surprising because it implied the reason for the failure to-date of the art to use interferon as an effective cancer therapy. While interferon should theoretically be an effective anti-cancer agent, interferon may also up-regulate expression of PD-L1, thus frustrating interferon's therapeutic effect.

Example 2—IFNα Induces PD-L1 Expression in a Dose-Dependent Manner

Here I had measured the expression of immune checkpoint PD-L1, micro-RNA (miR) and mRNA expression profiles after treatment with interferon alpha.

Materials & Methods: RT112, T24, UC3, and UC14 cells were cultured in media and then exposed for 6 hours to either control media, or media containing 1000 IU/ml of interferon alpha polypeptide. Expression of PD-L1 was evaluated by Western blot and quantitative real-time PCR using commercially available antibodies and primers. RNA was isolated from cells in culture with the MIRVANA™ kit (Thermo Fisher). mIRs were profiled in RT112 using TAQMAN™ Array Cards (A and B) (Thermo Fisher). Whole genome mRNA expression profiling was performed in RT112 and UC3 with Illumina HumanHT_12_v4 BEADCHIP™ arrays (47323 probes). All experiments were performed in triplicate to increase statistical reliability.

Figure 5:
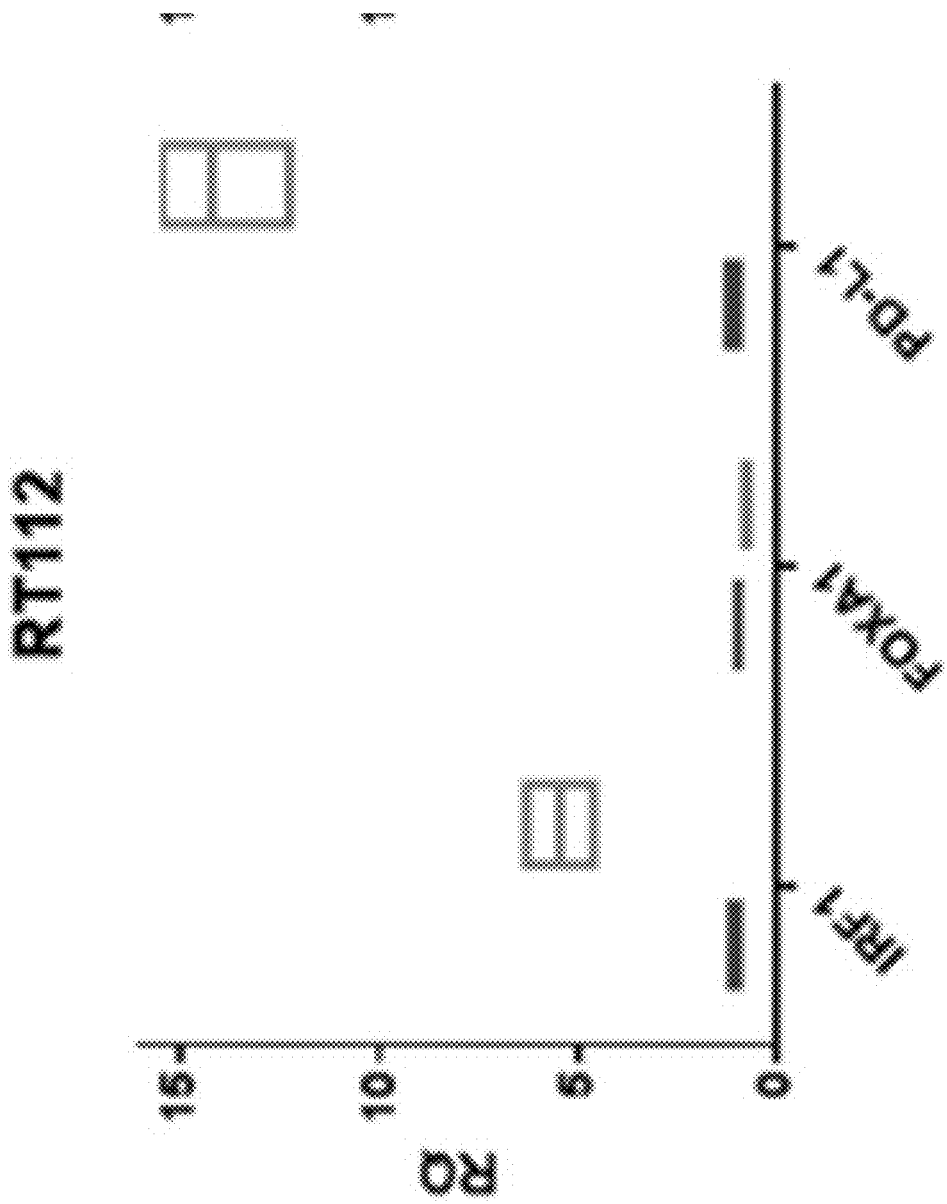
FIG. 5 measures expression in RT112 cells of IRF1, FOXA1 and PD-L1 in response to interferon exposure, see Example 2. IRF1 served as an interferon-stimulated gene control. FOXA1 is an example of a type I interferon regulated gene that did not change expression after interferon exposure.
Figure 6:
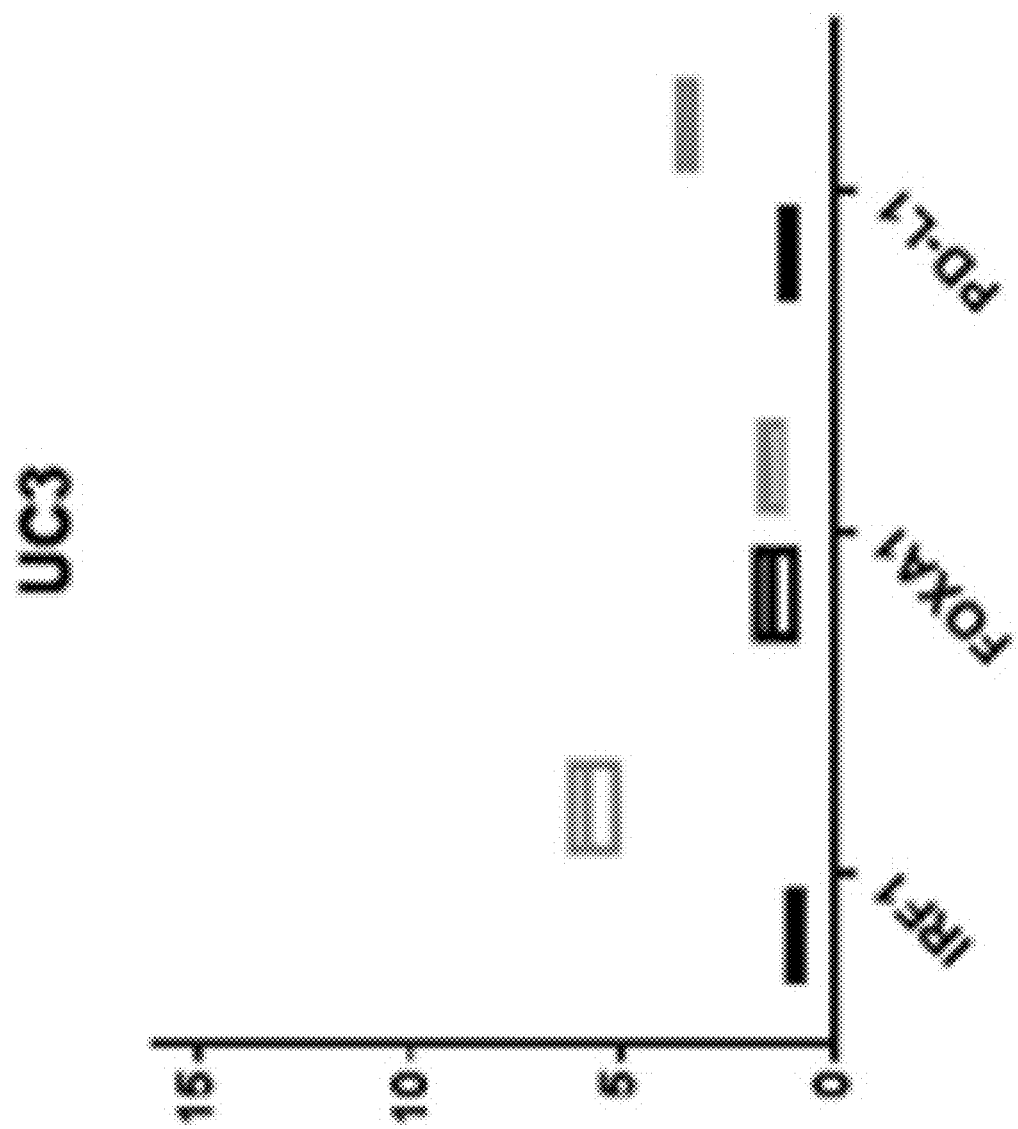
FIG. 6 measures expression in UC3 cells of IRF1, FOXA1 and PD-L1 in response to interferon exposure, see Example 2. IRF1 served as an interferon-stimulated gene control. FOXA1 is an example of a type I interferon regulated gene that did not change expression after interferon exposure.
Figure 7:
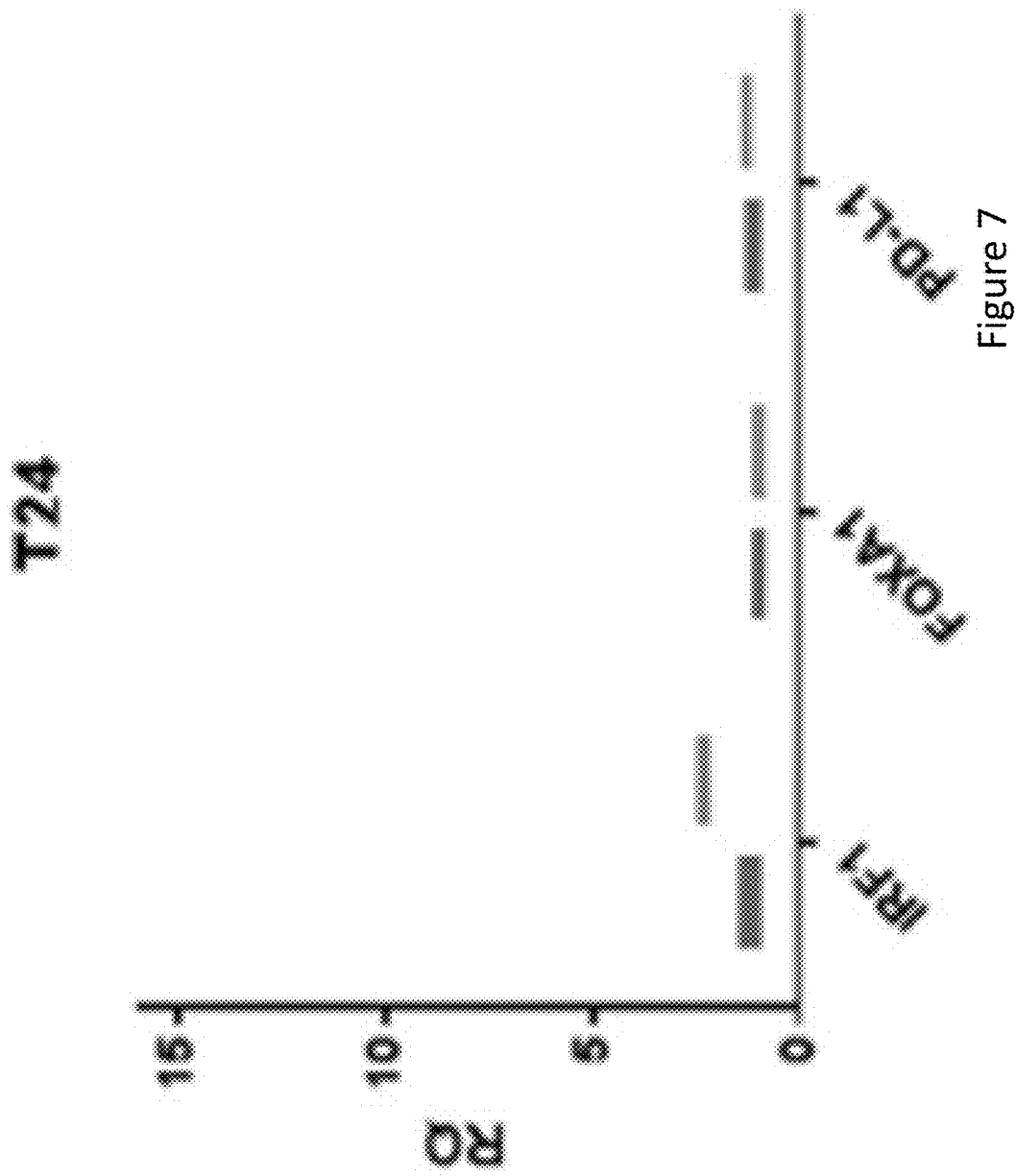
FIG. 7 measures expression in T24 cells of IRF1, FOXA1 and PD-L1 in response to interferon exposure, see Example 2. IRF1 served as an interferon-stimulated gene control. FOXA1 is an example of a type I interferon regulated gene that did not change expression after interferon exposure.
Figure 8:
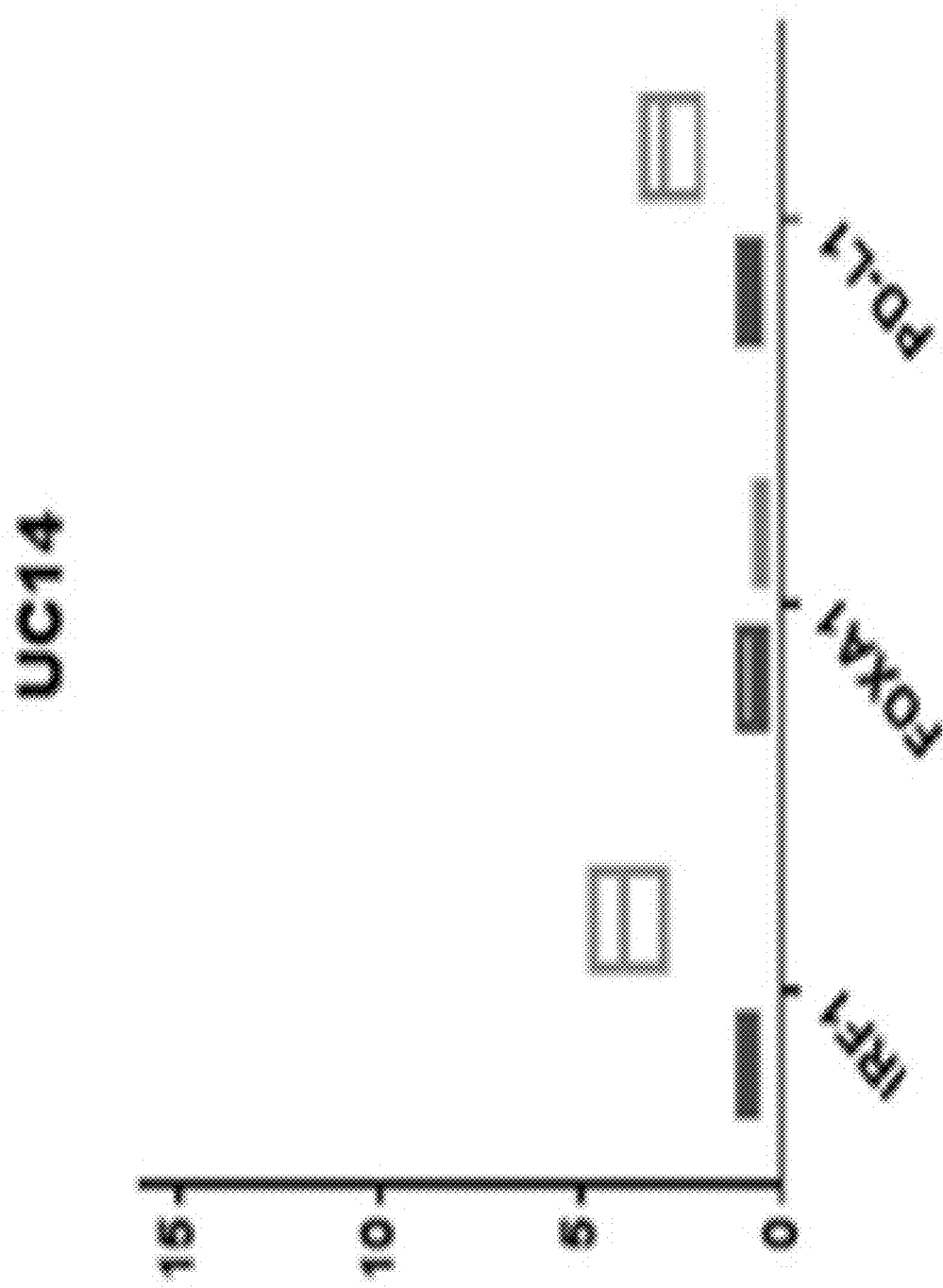
FIG. 8 measures expression in UC14 cells of IRF1, FOXA1 and PD-L1 in response to interferon exposure, see Example 2. IRF1 served as an interferon-stimulated gene control. FOXA1 is an example of a type I interferon regulated gene that did not change expression after interferon exposure.

Results: All cell lines up-regulated the expression PD-L1 in response to exposure to IFNa. This effect was most pronounced in RT112 cells, see FIG. 5, than in UC3 cells, FIG. 6. In contrast, the expression of three potential oncomIR regions was significantly down-regulated after exposure to IFNa in RT112:1233 cells ($p=0.0036$), 19b-1# ($p=0.0157$), and 222# ($p=0.0061$). Analyzing differentially-expressed genes with at least 2-fold differences in log (expression) (false discovery rate <0.001) after IFNa exposure, there were and 181 differentially expressed genes in the RT112 and UC3 cell lines, respectively. Top-ranked IFNa-induced genes in both cell lines included several that had not been previously described in bladder cancer, including IFIT2 (negative regulator of metastasis) and IFI27 (associated with sensitivity to TRAIL). IFNa-induced PD-L1 expression was also demonstrable on the mRNA gene chip with fold-changes paralleling real-time PCR data.

Conclusions: In a panel of cancer cell lines, IFNa exposure lead to significant increases in PD-L1 immune checkpoint expression. Array-based microRNA and mRNA profiling revealed novel potential mediators of IFNa response in bladder cancer. This bladder IFNa profile may be useful as an intermediate endpoint to measure response to adenoviral IFNa gene therapy. Future prediction of PD-L1 expression with IFNa therapy may lead to rational combination treatments utilizing immune checkpoint inhibitors.

Example 3—Murine Interferon Induces PD-L1 Expression

Materials and Methods: BBN972 and MB49 #1 (MB49-luc) cells were cultured, and then exposed to media containing from 0 (zero) to $1 \times 10^4$ international units of murine interferon. Subsequent expression of PD-L1 and (as a control) actin were measured.

Figure 9:
FIG. 9 is a photograph of a 6-lane PAGE gel. It measures the presence of PD-L1 polypeptide after exposing BBN972 cells to murine interferon. Lanes are (left to right) 0 (zero), $1\times10^0$, $1\times10^1$, $1\times10^2$, $1\times10^3$ and $1\times10^4$ international units interferon/mL of culture medium.
Figure 10:
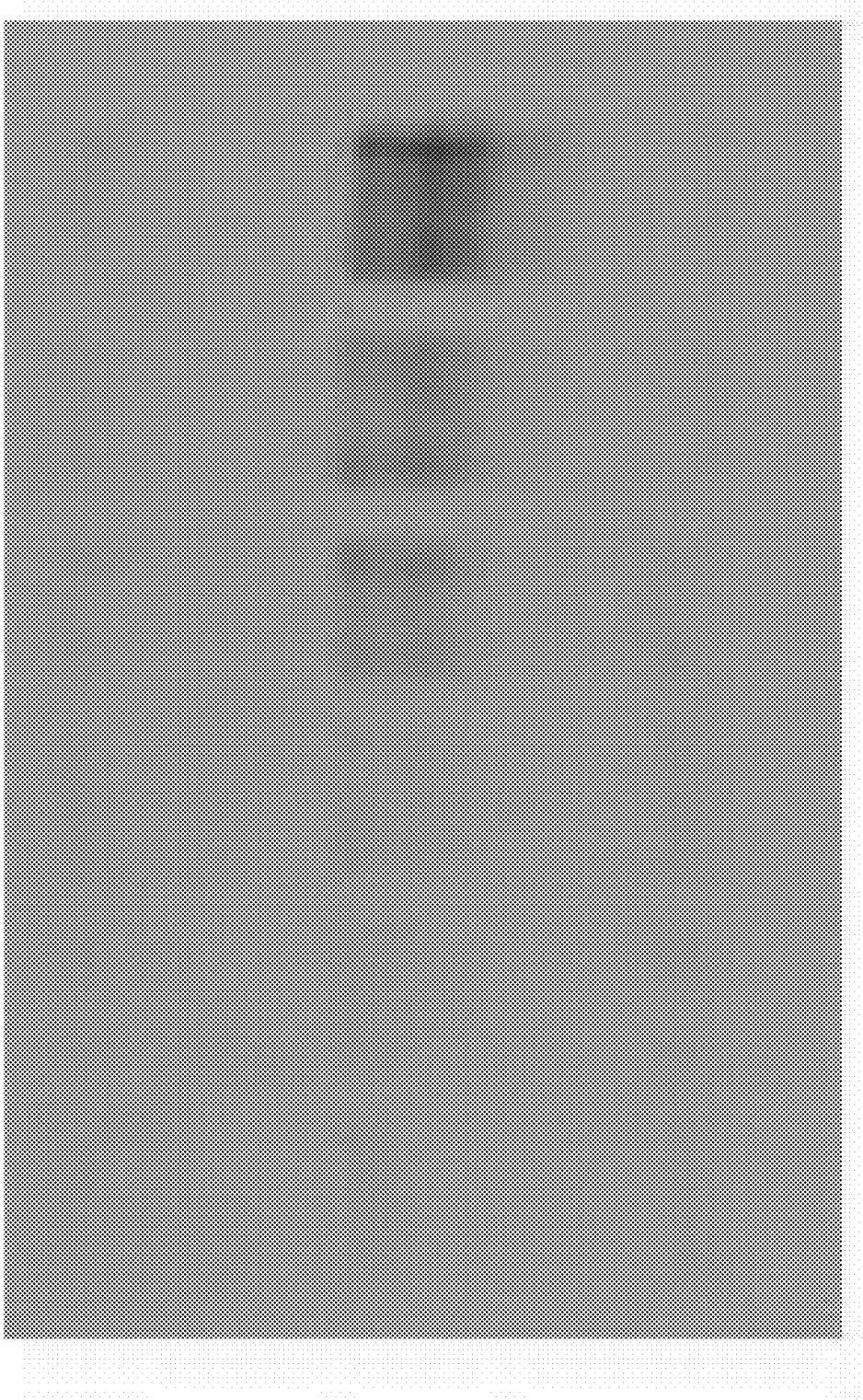
FIG. 10 is a photograph of a 6-lane PAGE gel. It measures the presence of PD-L1 polypeptide after exposing MB49 #1 (MB49-luc) cells to murine interferon. Lanes are (left to right) 0 (zero), $1\times10^0$, $1\times10^1$, $1\times10^2$, $1\times10^3$ and $1\times10^4$ international units interferon/mL of culture medium.
Figure 11:
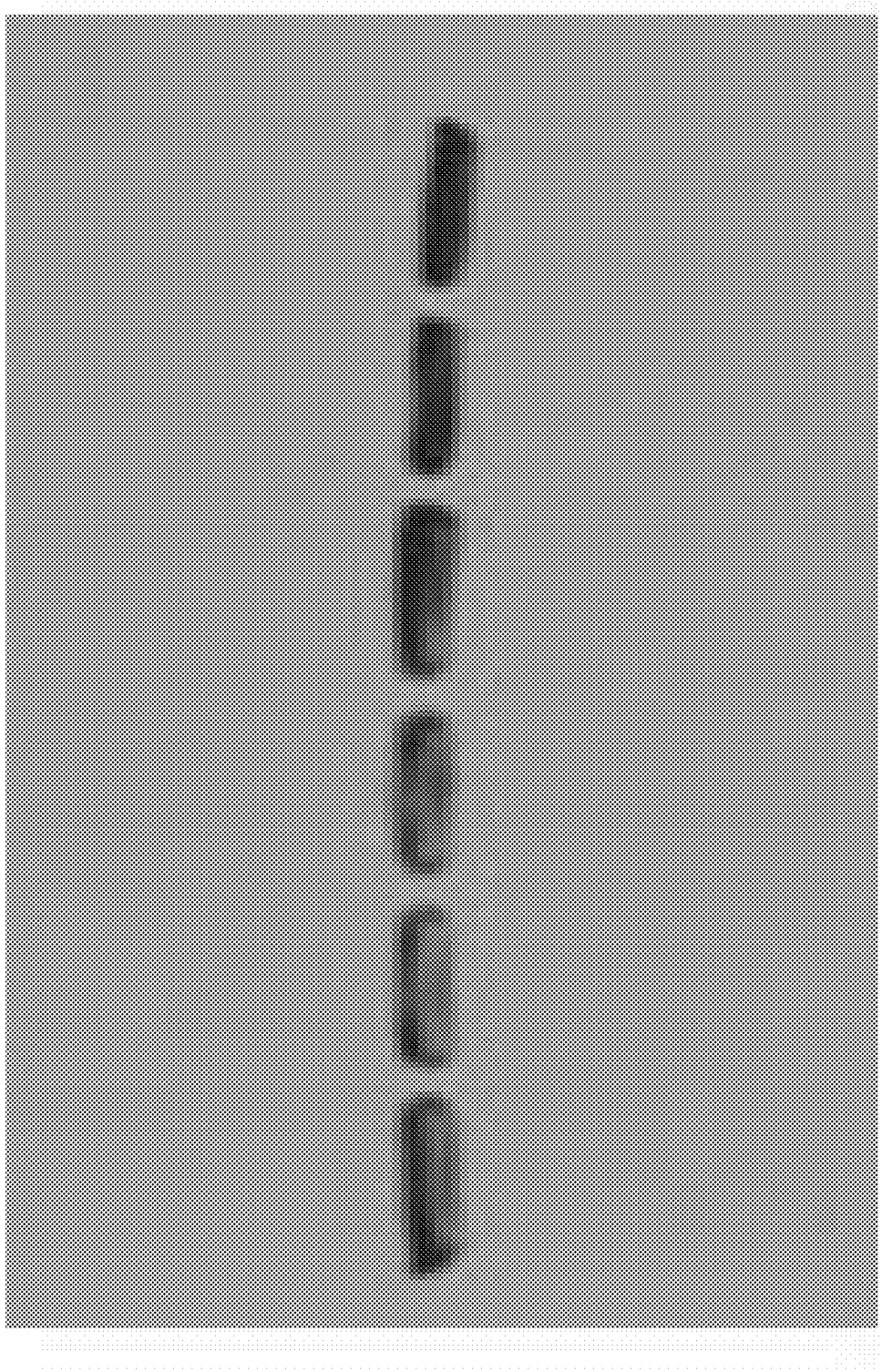
FIG. 11 is a photograph of a 6-lane PAGE gel. It measures the presence of actin polypeptide after exposing BBN972 cells to murine interferon. Lanes are (left to right) 0 (zero), $1\times10^0$, $1\times10^1$, $1\times10^2$, $1\times10^3$ and $1\times10^4$ international units interferon/mL of culture medium.
Figure 12:
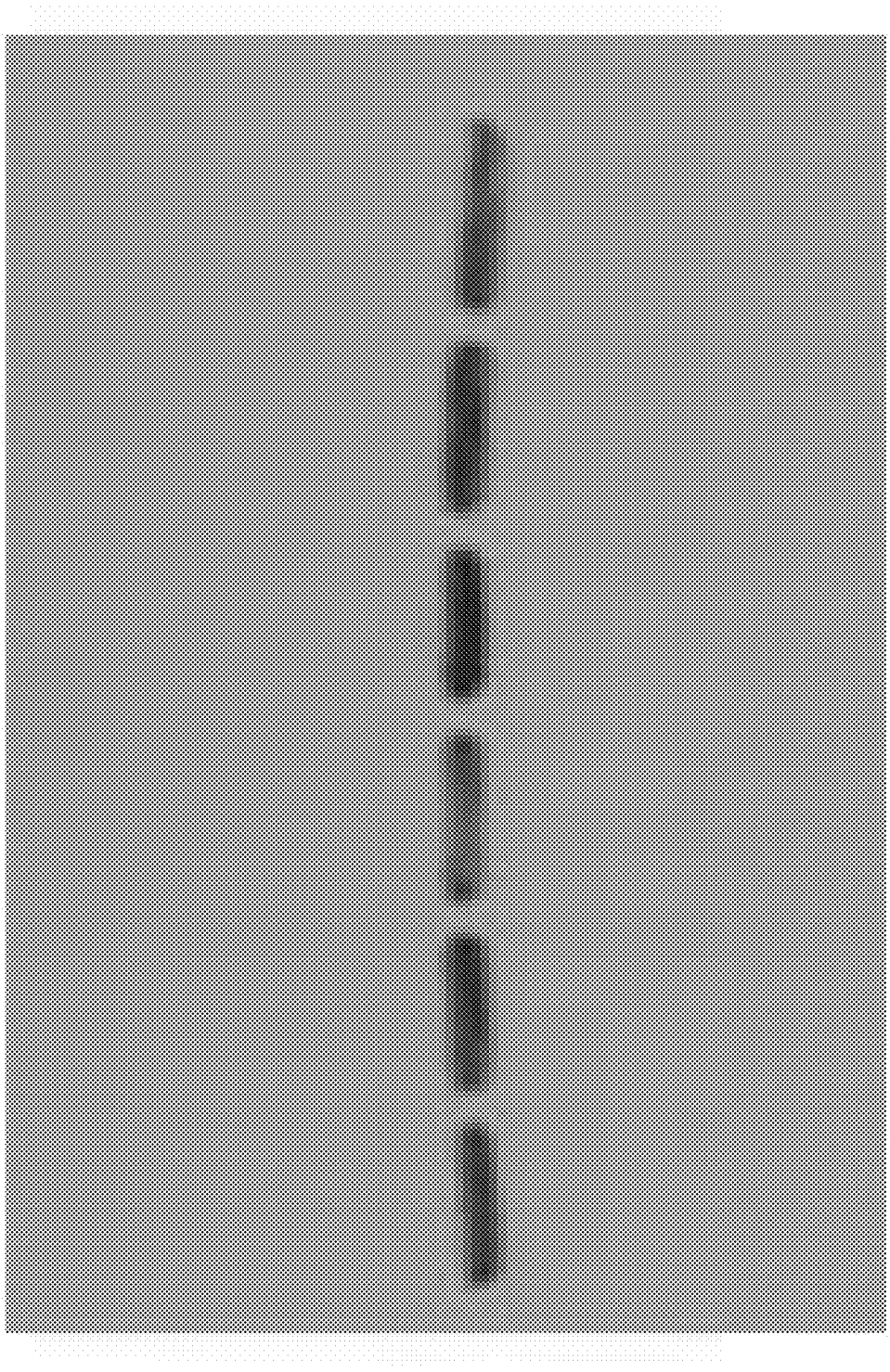
FIG. 12 is a photograph of a 6-lane PAGE gel. It measures the presence of actin polypeptide after exposing MB49 #1 cells to murine interferon. Lanes are (left to right) 0 (zero), $1\times10^0$, $1\times10^1$, $1\times10^2$, $1\times10^3$ and $1\times10^4$ international units interferon/mL of culture medium.

Results: Murine interferon had no effect on the expression of actin in either cell line. See FIGS. 11, 12. In contrast, Murine interferon had a marked, dose-dependent effect on PD-L1 expression. See FIGS. 9, 10.

Conclusions: These data show that the effect of interferon on PD-L1 expression is not limited to human interferon alpha 2a, nor indeed to human interferon. Rather, the effect of interferon on expression of PD-L1 appears to be generic to interferon generally.

Example 4—Polyinosinic:Polycytidylic Acid (Poly I:C) Induces PD-L1

Materials & Methods: The foregoing data indicate that interferon induces PD-L1 expression, does so in a dose-dependent manner, does so quickly, and does so apparently in response to interferon from different species. Given the effect regardless of the animal species from which the interferon was taken, I hypothesized that the effect might not be limited to interferon, and might be more generally provoked by immune stimulants of other types. To test the concept, I had evaluated Polyinosinic:polycytidylic acid (often abbreviated "poly I:C"). Poly I:C is an immunostimulant. It is used in the form of its sodium salt to simulate viral infections. Poly I:C is structurally similar to double-stranded RNA. dsRNA is present in some viruses. I had Poly I:C administered via intra-peritoneal injection to laboratory mice with implanted plc or ulc tumors.

Figure 13:
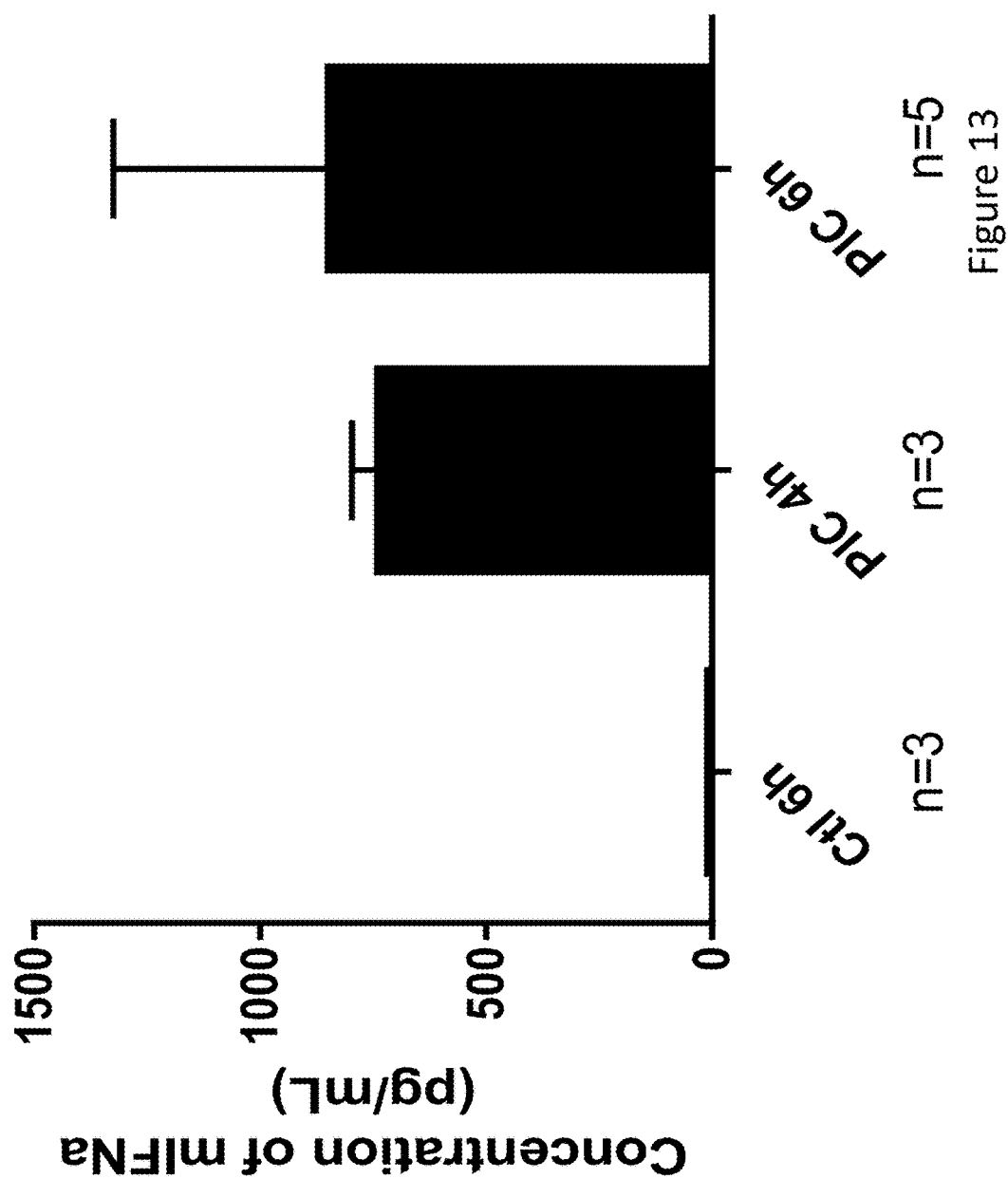
FIG. 13 measures serum interferon a in mice in response to intra-peritoneal injection of Poly I:C.
Figure 14:
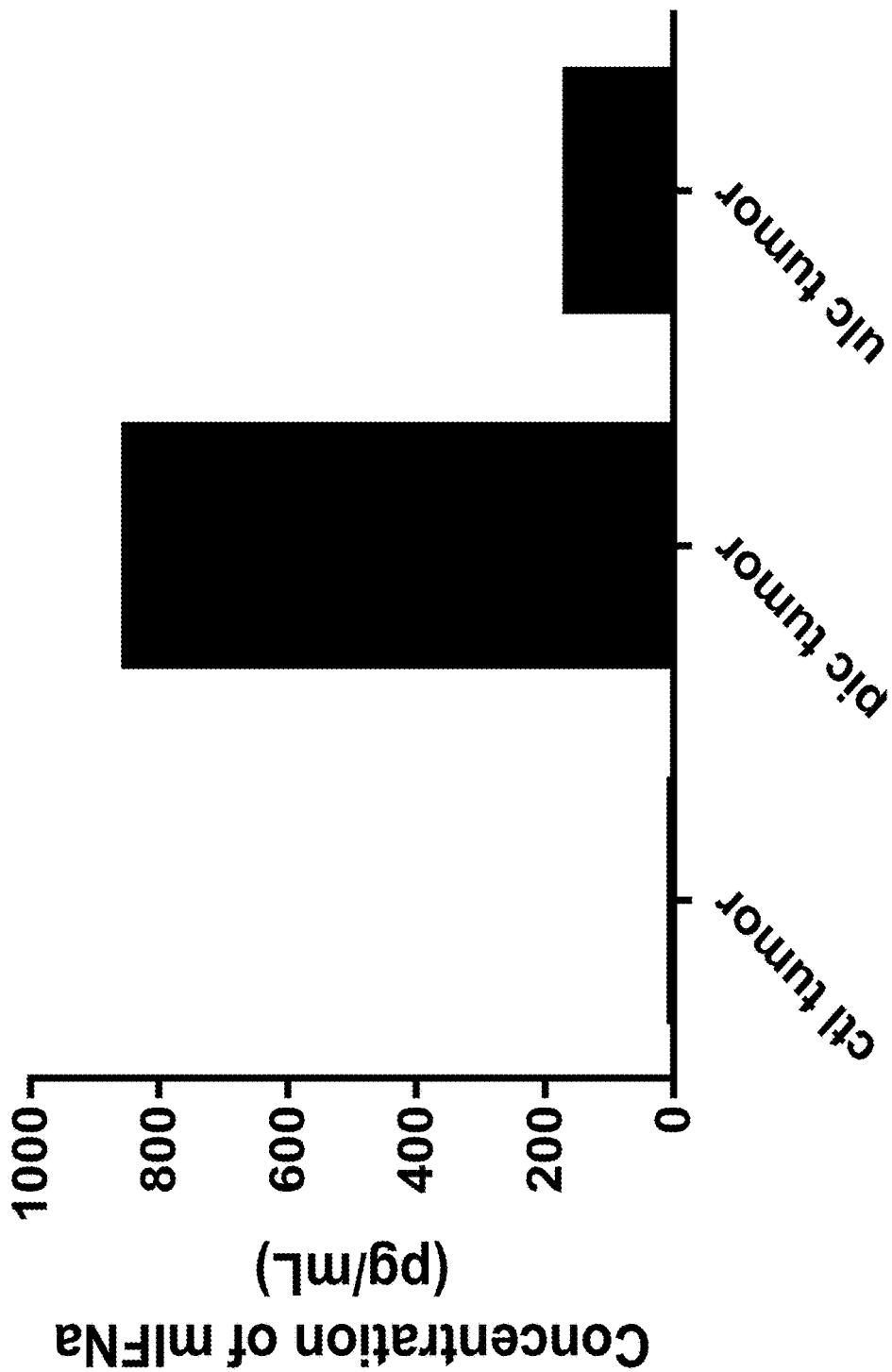
FIG. 14 measures serum interferon a in mice in response to intra-tumoral injection of Poly I:C at 6 hours.
Figure 15:
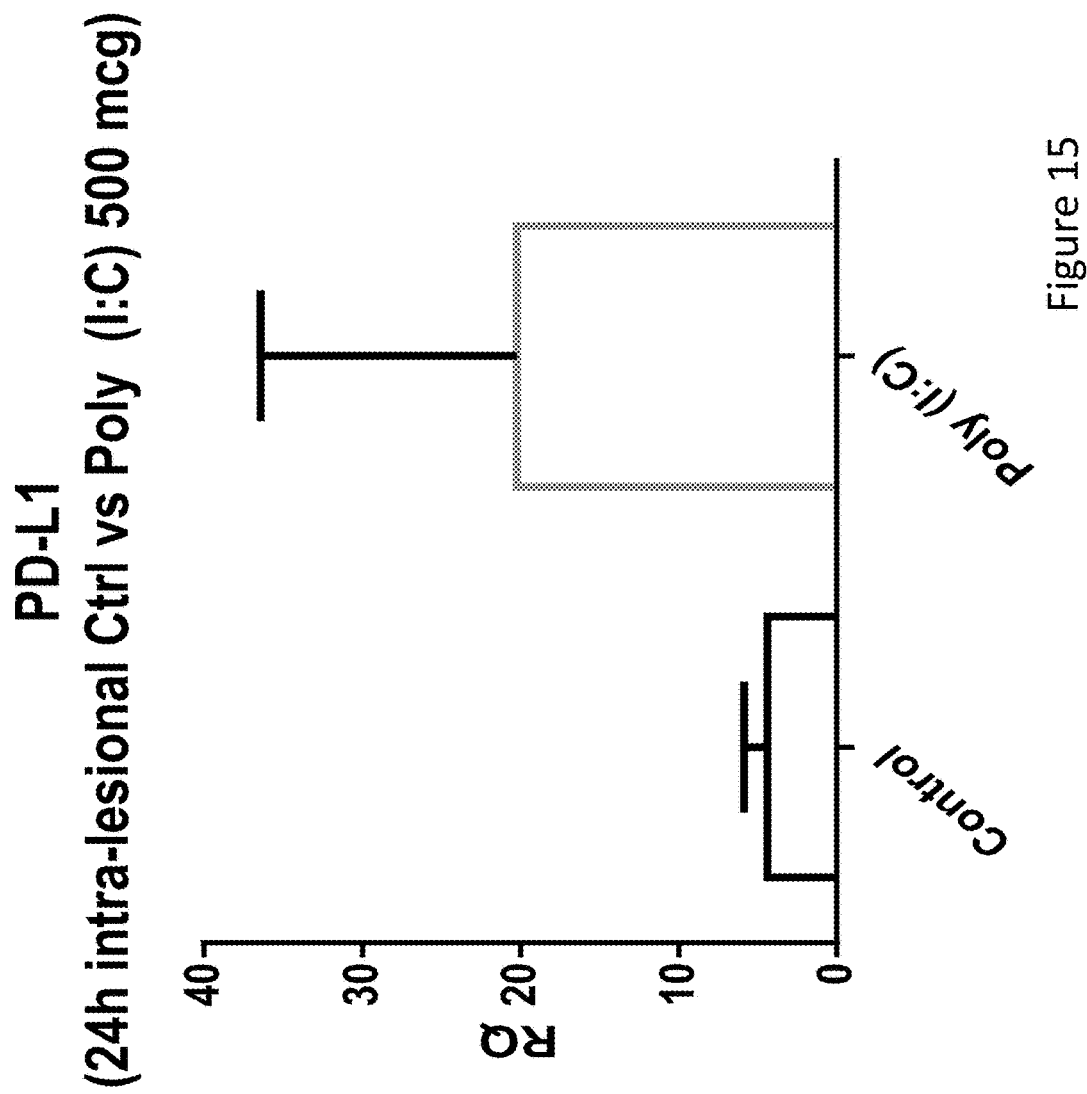
FIG. 15 measures PD-L1 expression intra-tumorally 24 hours after Poly I:C (500 mcg) intra-peritoneal injection.

Results. FIG. 13 shows that control mice (n=3) showed a de minimus baseline measure of serum interferon a. In contrast, intra-peritoneal injection of Poly I:C produces a time-dependent increase in serum interferon a. FIG. 14 shows results of intra-tumoral injection of Poly I:C at 6 hours. The data (n=1 for each series) show that intra-tumor interferon a increases significantly in plc tumors, increases somewhat in ulc tumors, and does not measurably increase in control tumors. FIG. 15 shows that Poly I:C (500 mcg) also induces (at 24 hours) PD-L1 expression intra-tumorally (Mann Whitney p=0.0495).

Conclusions: These data indicate that PD-L1 expression is induced not merely by interferon, but by Poly I:C, a compound which mimics dsRNA and which induces interferon expression.

Example 5—Interferon Viral Gene Therapy Induces PD-L1 in Humans

Materials & Methods: These data are taken from a human Phase II human clinical trial for INSTILADRIN™ replication-deficient adenoviral gene therapy vector carrying a human interferon alpha 2b transgene in patients unresponsive to or refractory after BCG therapy. That study plan has been published and is incorporated here by reference.

Figure 16:
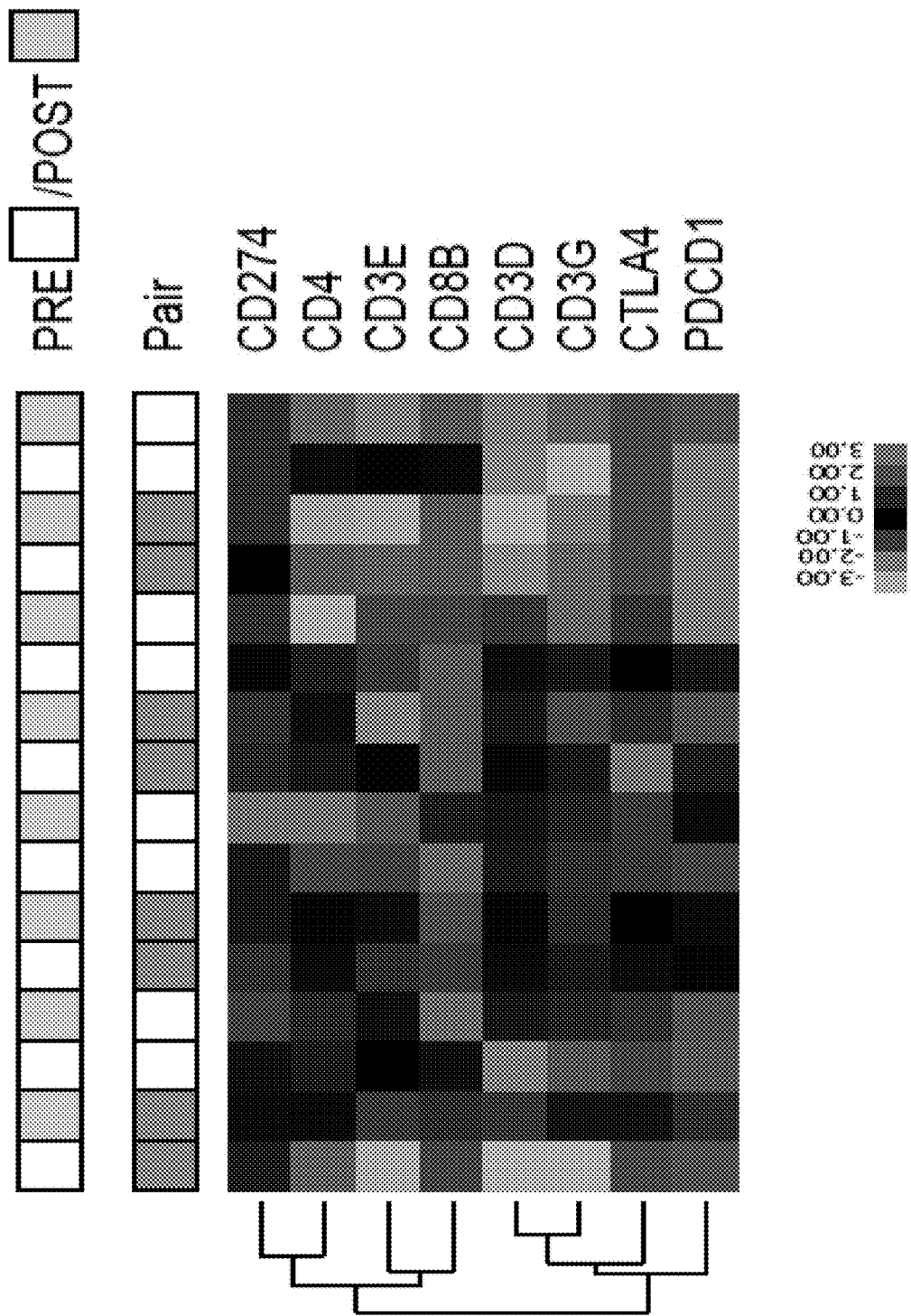
FIG. 16 shows RNA expression in humans treated with INSTILADRIN™ recombinant replication-deficient adenovirus gene therapy vector carrying a human interferon alpha 2B transgene.

Results: FIG. 16 shows RNA expression in eight (8) treatment cycles in humans treated with INSTILADRIN™ recombinant replication-deficient adenovirus gene therapy vector carrying a human interferon alpha 2B transgene. Odd (white color coded) columns measure RNA transcription before treatment; even (light blue color coded) columns measure after. RNA amounts are shown quantitatively, light green showing the least and light red the most. Columns 1 and 2 show PD-L1 RNA increasing from −2 before treatment to +2 after. Columns 3 and 4 similarly show PD-L1 RNA increasing from −2 before treatment to +3 after. In all, one third of the treatment pair show a significant increase in PD-L1 expression after treatment. Treatment also up-regulated other immune checkpoint markers.

Conclusions: These data show that one third of patients demonstrate induction of T-cell and immune checkpoint markers (including PD-L1) after treatment with interferon gene therapy.

Example 6—Combination Therapy Increases Survival

Materials & Methods: Female laboratory rats were inoculated with tumor cells, and the cells allowed to develop into measurable tumors. The rats were then treated with saline (control), IgG (as a control), anti-PD1 monoclonal antibody (monotherapy), Poly I:C (monotherapy to induce interferon expression) and a combination of Poly I:C and anti-PD1 monoclonal antibody (combination therapy).

Figure 17:
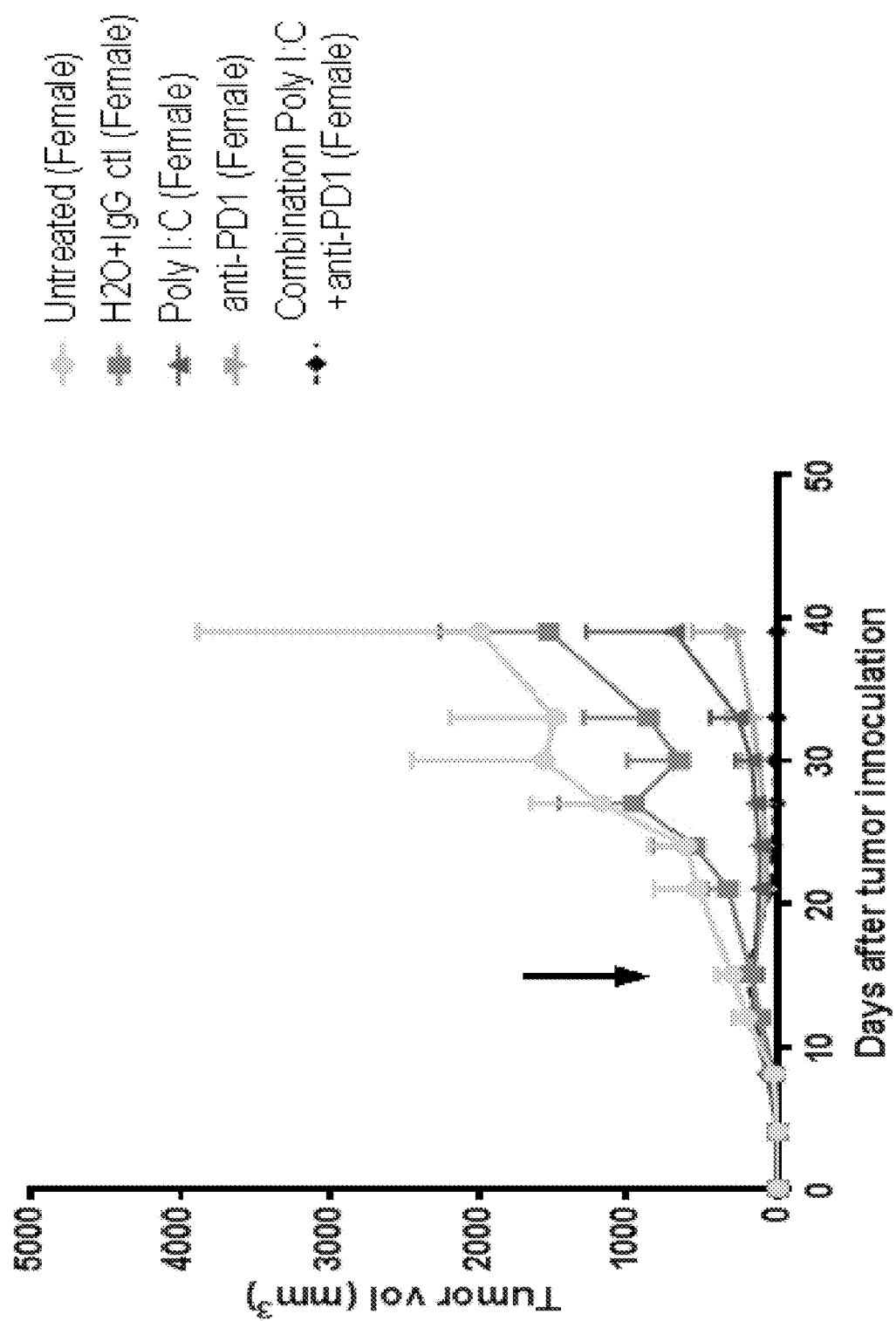
FIG. 17 shows MB49 tumor size vs time, for subcutaneous C57BL6/J tumors (n=5 female mice per group). Treatment is 200 mcg q3 days starting on day 10 after tumor implant. Error bard represent SEM.

Results: FIG. 17 shows MB49 tumor size vs time, for subcutaneous C57BL6/J tumors (n=5 female mice per group). Treatment is 200 mcg q3 days starting on day 10 after tumor implant. Error bard represent SEM. The highest (yellow) line, showing the largest tumor volume at day 40, is control group (all groups n=5, female-only). The next lowest (blue) line is the IgG control. The next lowest (red) line is Poly I:C. The next lowest (green) line is anti-PD1 Monoclonal antibody. The lowest (black) line, laying on the X axis itself, is combination therapy.

Figure 18:
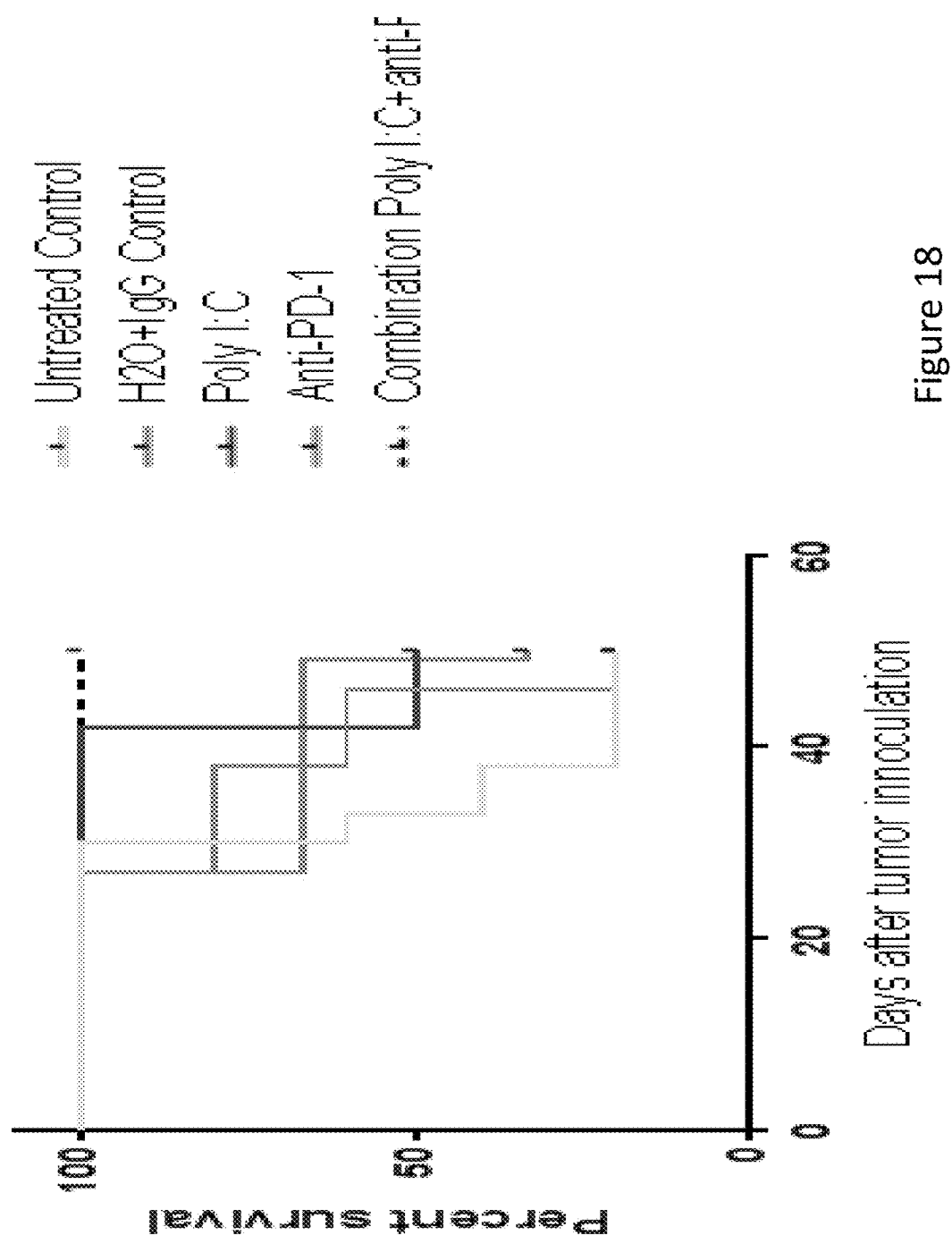
FIG. 18 shows a Kaplan-Meyer survival curve for female mice with inoculated tumors, treated with saline (lowermost line), IgG (next higher line), anti-PD1 monoclonal antibody (next higher line), Poly I:C (next higher line) and a combination of Poly I:C and anti-PD1 monoclonal antibody (highest line).

FIG. 18 shows a Kaplan-Meyer survival curve for female mice with inoculated tumors, treated with saline (lowermost line), IgG (next higher line), anti-PD1 monoclonal antibody (next higher line), Poly I:C (next higher line) and a combination of Poly I:C and anti-PD1 monoclonal antibody (highest line). These data show that combining an interferon-inducing agent (Poly I:C) and a PD1 inhibitor (an anti-PD1 monoclonal antibody) increases survival significantly: at 50 days, ~20% of control animal remain alive, 50% of Poly I:C animals remain alive, and 100% of combination treated animals remain alive.

Figure 19:
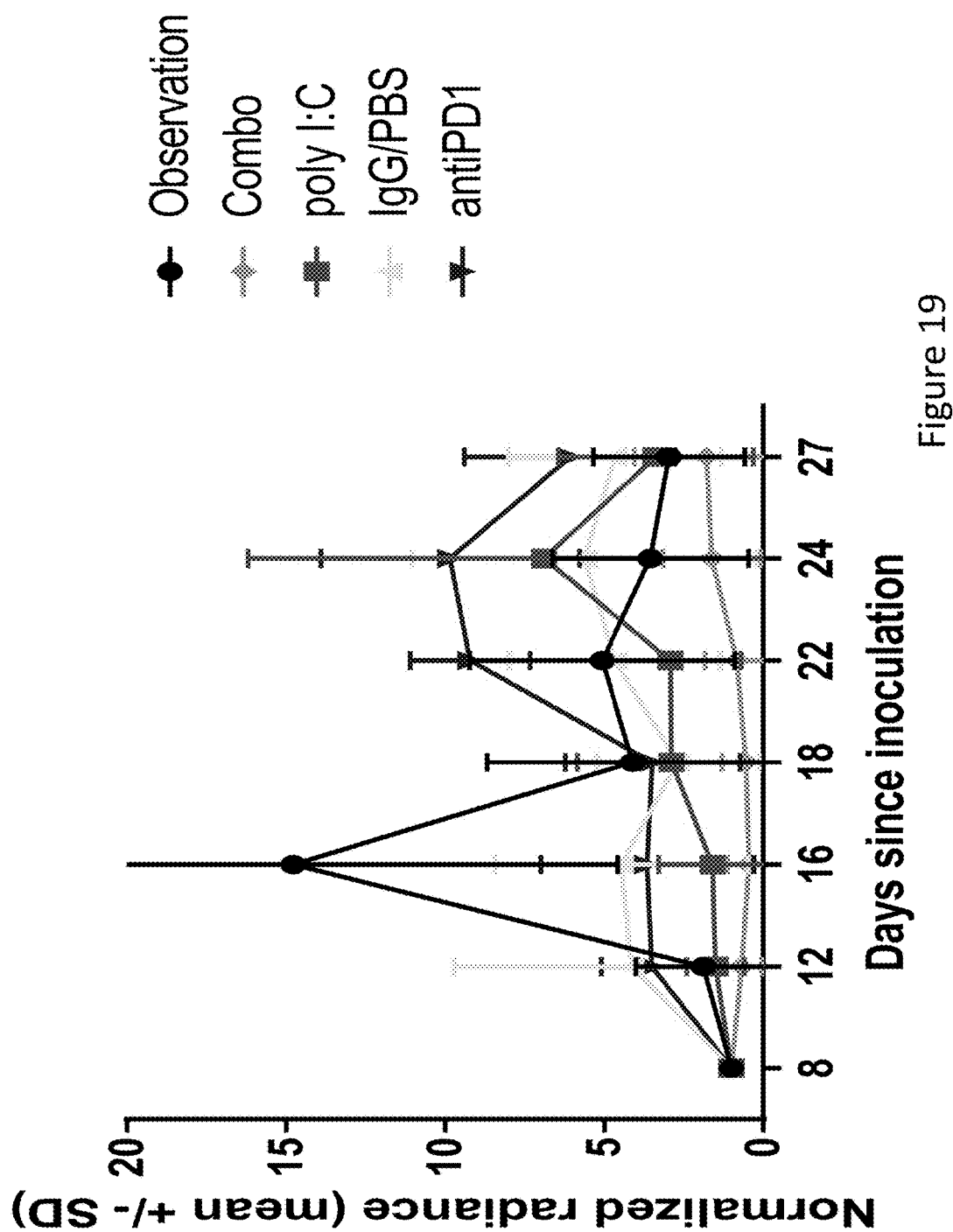
FIG. 19 compares normalized (mean+/−SD) radiance over time in male mice. Using a log-rank test, these data show combination therapy superior to IgG control (p=0.06), superior to Poly I:C monotherapy (p=0.32), and superior to anti-PD1 monoclonal antibody (p=0.14).

FIG. 19 compares normalized (mean+/−SD) radiance over time in male mice. Using a log-rank test, these data show combination therapy superior to IgG control (p=0.06), superior to Poly I:C monotherapy (p=0.32), and superior to anti-PD1 monoclonal antibody (p=0.14).

Figure 20:
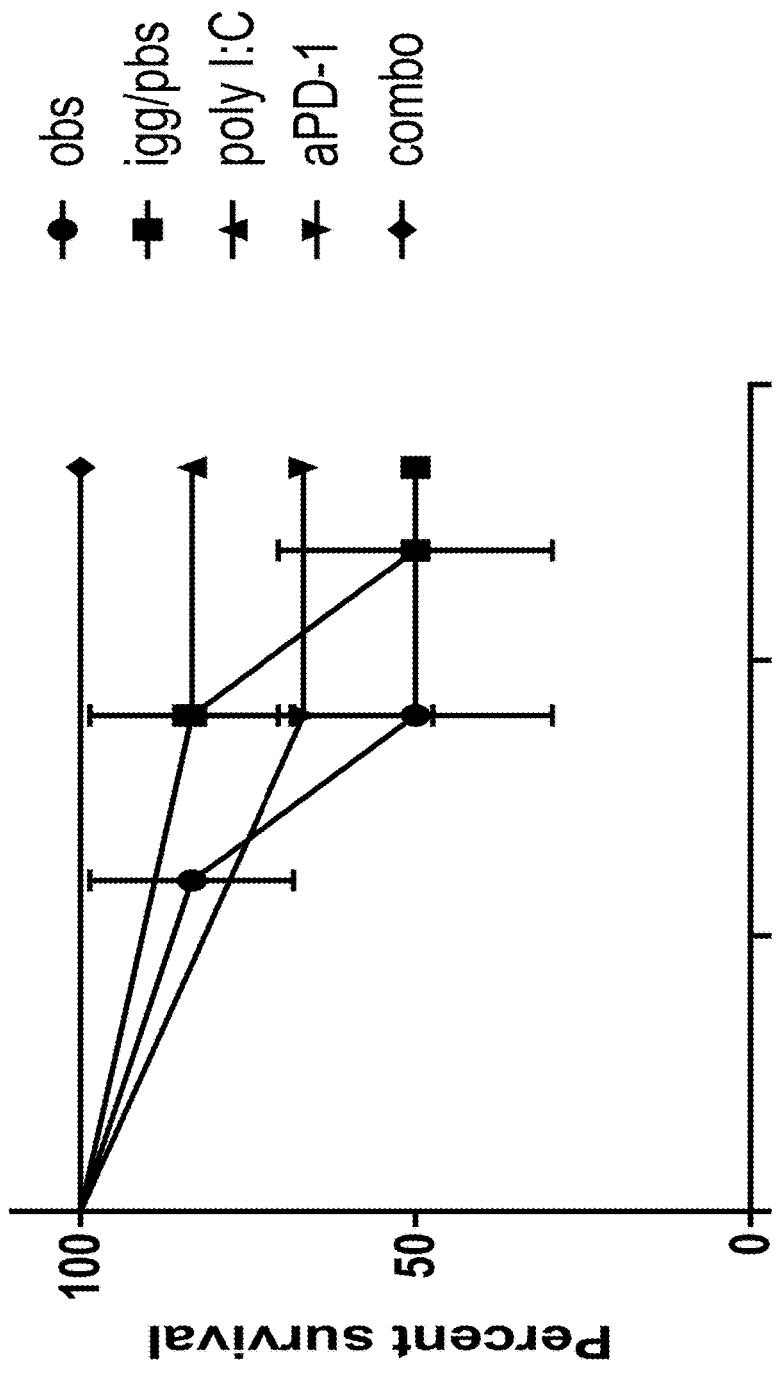
FIG. 20 shows "survival portions," i.e., data showing the survival of propensity to survive over time, in male mice treated per FIG. 19.

FIG. 20 shows "survival portions," i.e., data showing the survival of propensity to survive, over time.

Conclusions: These data show combination therapy synergistically effective, imparting a more than merely additive effect.

Example 7—Superficial Spreading Melanoma

Materials & Methods: A human patient diagnosed with superficial spreading melanoma is treated by wide local excision and sentinel node biopsy to confirm lack of spread of the disease to the lymph system or distal organs. The patient is then treated with a combination of INSTI-LADRIN™ and KEYTRUDA™. Treatment is initiated as soon as practical after surgical resection.

INSTILADRIN™ brand adenovirus is a replication-deficient, recombinant adenoviral gene therapy vector bearing an interferon alpha 2b transgene. The manufacture of such gene therapy vectors is described in, e.g., Muralidhara Ramachandra et al., Selectively Replicating Viral Vector, U.S. Pat. No. 7,691,370. The isolation of interferon transgenes is described in e.g., Charles Weissmann, DNA Sequences, Recombinant DNA Molecules and Processes for Producing Human Interferon-Like Polypeptides, U.S. Pat. No. 6,835,557.

KEYTRUDA™ brand pembrolizumab is a humanized monoclonal anti-programmed cell death-1 (PD-1) antibody (IgG4/kappa isotype with a stabilising sequence alteration in the Fc region).

INSTILADRIN™ is provided in single-dose vials. One dose of INSTILADRIN™ is reconstituted in sterile saline for injection and administered subcutaneously locally to the excision site. Administration is repeated once every four weeks. One vial of KEYTRUDA™ powder contains 50 mg of pembrolizumab. KEYTRUDA™ is administered as an intravenous infusion over 30 minutes, repeated every 3 weeks, and patients are treated until disease progression or unacceptable toxicity. Atypical responses (i.e., an initial transient increase in tumour size or small new lesions within the first few months followed by tumour shrinkage) may be observed. It is preferred to continue treatment for clinically-stable patients with initial evidence of disease progression until disease progression is confirmed.

Test subjects are enrolled and then assigned to a treatment group: excision followed by KEYTRUDA™ only, excision followed by INSTILADRIN™ only, excision followed by KEYTRUDA™ and INSTILADRIN™ concomitantly, excision followed by INSTILADRIN™ and NSAID (a COX-2 inhibitor), and excision followed by KEYTRUDA™ and INSTILADRIN™ and NSAID concomitantly.

Results: The primary efficacy outcome measures are progression free survival (as assessed by e.g., an Integrated Radiology and Oncology Assessment review using Response Evaluation Criteria in Solid Tumours [RECIST]), overall survival, and sentinel node biopsy. Other efficacy outcome measures may be overall response rate and response duration. Subsequent sentinel node biopsy is expected to show no spread of the disease.

I expect that administration of INSTILADRIN™ with COX-2 inhibitor will demonstrate superior efficacy to INSTILADRIN™ only. I expect that administration of KEYTRUDA™ and INSTILADRIN™ concomitantly will demonstrate superior efficacy outcome measures as compared to administration of either agent alone, and I expect this benefit to be more than merely additive. I expect that administration of KEYTRUDA™ and INSTILADRIN™ and NSAID concomitantly will demonstrate superior efficacy outcome measures as compared to administration of KEYTRUDA™ alone or INSTILADRIN™ and NSAID alone, and I expect this benefit to be more than merely additive.

Example 8—Superficial Spreading Melanoma

Materials & Methods: KEYTRUDA™ as in the foregoing example.

As a source of interferon, SYLATRON™ PEG-ylated interferon alpha 2b, administered subcutaneously at 6 mcg/kg once weekly for 8 doses (induction), followed by 3 mcg/kg once weekly for up to 5 years (maintenance). If SYLATRON™ dosage modification is required during weeks 1-8 of treatment (induction) because of adverse reactions, a 3-step decrease from original dosage (6 mcg/kg once weekly) is preferred (i.e., decrease dosage to 3 mcg/kg once weekly; if needed, decrease to 2 mcg/kg once weekly; then, if needed, further decrease to 1 mcg/kg once weekly). If dosage modification required during weeks 9-260 of treatment (maintenance) because of adverse reactions, a 2-step decrease from original dosage (3 mcg/kg once weekly) recommended (i.e., decrease dosage to 2 mcg/kg once weekly; if needed, decrease to 1 mcg/kg once weekly).

Test subjects are enrolled and then assigned to a treatment group: excision followed by KEYTRUDA™ only, excision followed by SYLATRON™ only, excision followed by KEYTRUDA™ and SYLATRON™ concomitantly, excision followed by SYLATRON™ and NSAID (a COX-2 inhibitor), and excision followed by KEYTRUDA™ and SYLATRON™ and NSAID concomitantly.

Results: The primary efficacy outcome measures are progression free survival (as assessed by e.g., an Integrated Radiology and Oncology Assessment review using Response Evaluation Criteria in Solid Tumours [RECIST]), overall survival, and sentinel node biopsy. Other efficacy outcome measures may be overall response rate and response duration. Subsequent sentinel node biopsy is expected to show no spread of the disease.

I expect that administration of SYLATRON™ with COX-2 inhibitor will demonstrate superior efficacy to SYLATRON™ only. I expect that administration of KEYTRUDA™ and SYLATRON™ concomitantly will demonstrate superior efficacy outcome measures as compared to administration of either agent alone, and I expect this benefit to be more than merely additive. I expect that administration of KEYTRUDA™ and SYLATRON™ and NSAID concomitantly will demonstrate superior efficacy outcome measures as compared to administration of KEYTRUDA™ alone or SYLATRON™ and NSAID alone, and I expect this benefit to be more than merely additive.

Example 9—Non-Small Cell Lung Cancer

Materials & Methods: Pharmaceutical Agents as per Example 7 above. Human test subjects are diagnosed as having Non-Small-Cell Lung Carcinoma. Patients are screened according to Greene, Frederick L., *Cancer Staging Manual* (American Joint Committee on Cancer, publ., 6th edition) to assure that comparable test subjects have comparable disease. Test subjects are screened for treatment based on the tumor expression of PD-L1, expression confirmed by a validated test.

The recommended dose of KEYTRUDA is: 200 mg for NSCLC that has not been previously treated with chemotherapy, and 2 mg/kg for NSCLC that has been previously treated with chemotherapy or for melanoma.

INSTILADRIN™ is administered by intra-pleaural infusion. This method is illustrated in United States Patent publication US2014/17202 at FIG. 2.

Test subjects are enrolled and then assigned to a treatment group: KEYTRUDA™ only, INSTILADRIN™ only, KEYTRUDA™ and INSTILADRIN™ concomitantly, INSTILADRIN™ and NSAID (a COX-2 inhibitor), and KEYTRUDA™ and INSTILADRIN™ and NSAID concomitantly.

Results: The primary efficacy outcome measures are progression free survival, overall survival, and sentinel node biopsy. Other efficacy outcome measures may be overall response rate and response duration. Subsequent sentinel node biopsy is expected to show no spread of the disease.

I expect that administration of INSTILADRIN™ with COX-2 inhibitor will demonstrate superior efficacy to INSTILADRIN™ only. I expect that administration of KEYTRUDA™ and INSTILADRIN™ concomitantly will demonstrate superior efficacy outcome measures as compared to administration of either agent alone, and I expect this benefit to be more than merely additive. I expect that administration of KEYTRUDA™ and INSTILADRIN™ and NSAID concomitantly will demonstrate superior efficacy outcome measures as compared to administration of KEYTRUDA™ alone or INSTILADRIN™ and NSAID alone, and I expect this benefit to be more than merely additive.

SUMMARY

The above Examples discuss treating certain cancers. Our discovery, however, may be more generally used to treat any condition which benefits from interferon signaling, and which suffers from over-expression of CD279.

In the appended claims, I use the term "treat" not to require complete cure, but to ameliorate. For example, "treating" cancer may be achieved by completely eliminating the cancer, and also by, for example, slowing tumor growth, reducing the risk of mortality or slowing disease progression when compared to patients who do not have such treatment.

Given our disclosure here, the artisan can readily see specific applications or variants of it. For example, while the above discussion mentions specific species of human interferon, other species and interferon derivatives or analogs which function similarly will provide the same benefit. Thus, I intend the legal coverage of our patent to be determined not by the Examples I discuss, but by the appended legal claims and permissible equivalents thereof When the appended legal claims refer to treating at about "the same time," see e.g., original claim 3, this requires the two compounds work in the patient at the same time. It does not require contemporaneous administration. Thus, one could administer the first agent a week after administering the second agent, if the effect of the second agent persists for at least a week.

The foregoing disclosure thus describes a method of treating a human patient with interferon comprising:
a. diagnosing in a human patient a condition which may be treated with interferon, and then
b. administering a first agent, the first agent able to increase the human patient's level of interferon in an amount sufficient to affect the function of a first human immune system checkpoint, whereby the checkpoint would decrease an immune function, and
c. administering to the human a second agent which affects the function of a second human immune system checkpoint, the second agent administered in an amount effective to substantially ameliorate the decrease in immune function which the first agent would have on said first human immune system checkpoint,
whereby the second compound substantially ameliorates the decrease in the immune function which would be caused by the first agent.

I claim:
1. A method of treating a human patient with interferon comprising:
   a. diagnosing in a human patient a cancer which may be treated with interferon, and then
   b. administering to the human patient interferon or an agent which induces interferon in a therapeutically effective amount, wherein interferon up-regulates programmed death protein ligand (PD-L1), and
   c. administering to the human a monoclonal antibody against programmed cell death protein 1, the monoclonal antibody against programmed cell death protein 1 administered in an amount effective to ameliorate the decrease in T cell function which interferon would cause,
whereby the monoclonal antibody against programmed cell death protein 1 ameliorates the decrease in T cell function caused by interferon.

2. A method consisting essentially of the method of claim 1.

3. The method of claim 1, where the patient is treated with interferon and the monoclonal antibody against programmed cell death protein 1 at about the same time.

4. The method of claim 1, where the interferon comprises exogenously-produced interferon polypeptide.

5. The method of claim 1, where the agent induces the patient to endogenously express interferon.

6. The method of claim 5, where the agent is a vector carrying an expressible interferon transgene.

7. The method of claim 5, where the agent is selected from the group consisting of microbial antigen, viral antigen and microbial or viral antigen analog.

8. The method of claim 7, where the agent comprises viral antigen analog comprising Poly I:C.

9. The method of claim 7, where the agent comprises bacterial antigen.

10. The method of claim 7, where the agent comprises viral antigen.

11. The method of claim 10, where the agent comprises antigenic virus.

12. The method of claim 1, where interferon is Type I interferon.

13. The method of claim 12, where the Type I interferon comprises interferon alpha.

14. The method of claim 12, where the Type I interferon comprises interferon beta.

15. A method of treating a human patient with interferon comprising: administering to the human patient a therapeutically-effective amount of interferon or an agent which induces interferon, wherein interferon up-regulates programmed death protein ligand (PD-L1), and administering a monoclonal antibody against programmed cell death protein 1 in an amount effective to ameliorate the T cell suppressing effect of interferon.

16. The method of claim 15, where the agent induces the patient to endogenously express interferon comprises inducing expression of a therapeutically-effective amount of interferon.

* * * * *